US008697717B2

(12) United States Patent
Van Emelen et al.

(10) Patent No.: US 8,697,717 B2
(45) Date of Patent: Apr. 15, 2014

(54) INHIBITORS OF HISTONE DEACETYLASE

(71) Applicant: Janssen Pharmaceutica, N.V., Beerse (BE)

(72) Inventors: Kristof Van Emelen, Sint-Niklaas (BE); Marc Gustaaf Celine Verdonck, Gierle (BE); Sven Franciscus Anna Van Brandt, Nijlen (BE); Patrick Rene Angibaud, Fontaine-Bellenger (FR); Lieven Meerpoel, Beerse (BE); Alexey Borisovich Dyatkin, Maple Glen, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/887,681

(22) Filed: May 6, 2013

(65) Prior Publication Data

US 2013/0245034 A1    Sep. 19, 2013

Related U.S. Application Data

(62) Division of application No. 12/560,657, filed on Sep. 16, 2009, now Pat. No. 8,455,498, which is a division of application No. 10/507,785, filed as application No. PCT/EP03/02515 on Mar. 11, 2003, now Pat. No. 7,615,553.

(60) Provisional application No. 60/363,799, filed on Mar. 13, 2002.

(51) Int. Cl.
C07D 471/10    (2006.01)
A61K 31/438    (2006.01)

(52) U.S. Cl.
USPC ............................................. 514/278; 546/20

(58) Field of Classification Search
USPC ................................................ 546/20; 514/278
See application file for complete search history.

(56) References Cited

U.S. PATENT DOCUMENTS

| | | | |
|---|---|---|---|
| 3,331,845 A | 7/1967 | Tomcufcik et al. | |
| 3,459,731 A | 8/1969 | Gramera et al. | |
| 3,966,743 A | 6/1976 | Berger et al. | |
| 3,979,390 A * | 9/1976 | Sasajima et al. | 544/392 |
| 4,049,811 A | 9/1977 | Berger et al. | |
| 4,348,401 A | 9/1982 | Friebe et al. | |
| 4,455,422 A | 6/1984 | Banno et al. | |
| 5,025,012 A | 6/1991 | Miura et al. | |
| 5,147,876 A | 9/1992 | Mizuchi et al. | |
| 5,338,738 A | 8/1994 | Matson et al. | |
| 5,342,846 A | 8/1994 | Singh et al. | |
| 5,780,454 A | 7/1998 | Adams et al. | |
| 5,789,412 A | 8/1998 | Halazy et al. | |
| 5,952,349 A | 9/1999 | Asberom et al. | |
| 6,066,730 A | 5/2000 | Adams et al. | |
| 6,083,903 A | 7/2000 | Adams et al. | |
| 6,294,538 B1 | 9/2001 | Mylari | |
| 6,518,283 B1 | 2/2003 | Langham et al. | |
| 6,589,950 B1 | 7/2003 | Collingwood et al. | |
| 6,897,307 B2 | 5/2005 | Ciszewski et al. | |
| 7,205,304 B2 | 4/2007 | Van Emelen et al. | |
| 7,446,109 B2 | 11/2008 | Van Emelen et al. | |
| 7,501,417 B2 | 3/2009 | Van Emelen et al. | |
| 7,541,369 B2 | 6/2009 | Angibaud et al. | |
| 7,592,450 B2 | 9/2009 | Van Emelen | |
| 7,615,553 B2 | 11/2009 | Van Emelen et al. | |
| 7,704,998 B2 | 4/2010 | Van Emelen et al. | |
| 7,709,487 B2 | 5/2010 | Van Emelen et al. | |
| 7,767,679 B2 | 8/2010 | Van Emelen et al. | |
| 7,816,363 B2 | 10/2010 | Angibaud et al. | |
| 7,834,011 B2 | 11/2010 | Roux et al. | |
| 7,834,025 B2 | 11/2010 | Angibaud et al. | |
| 7,884,105 B2 | 2/2011 | Van Emelen | |
| 7,888,360 B2 | 2/2011 | Angibaud et al. | |
| 8,455,498 B2 | 6/2013 | Van Emelen et al. | |
| 2002/0032195 A1 | 3/2002 | Breitfelder et al. | |
| 2004/0248897 A1 | 12/2004 | Priepke et al. | |

(Continued)

FOREIGN PATENT DOCUMENTS

| | | |
|---|---|---|
| CA | 2491131 | 1/2004 |
| CA | 2518950 | 2/2005 |

(Continued)

OTHER PUBLICATIONS

Janssen, CAPLUS Abstract 63:54675 (1965).*
U.S. Appl. No. 10/506,998: Non-Final Office Action, dated Jun. 19, 2007, 7 pages.
U.S. Appl. No. 10/506,998: Non-Final Office Action, dated Oct. 2, 2008, 5 pages.
U.S. Appl. No. 10/507,084: Non-Final Office Action, dated Feb. 25, 2008, 5 pages.

(Continued)

Primary Examiner — Deepak Rao
(74) Attorney, Agent, or Firm — Baker & Hostetler LLP

(57) ABSTRACT

This invention comprises the novel compounds of formula (I)

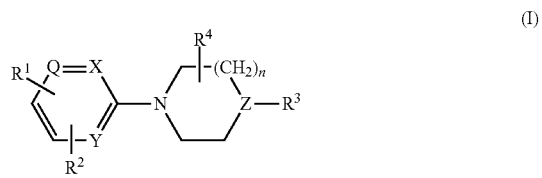

wherein n, $R^1$, $R^2$, $R^3$, $R^4$, Q, X, Y, Z and

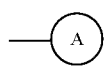

have defined meanings, having histone deacetylase inhibiting enzymatic activity; their preparation, compositions containing them and their use as a medicine.

13 Claims, No Drawings

(56) References Cited

U.S. PATENT DOCUMENTS

| | | |
|---|---|---|
| 2005/0080258 A1 | 4/2005 | Davis et al. |
| 2005/0107384 A1 | 5/2005 | Angibaud et al. |
| 2005/0171347 A1 | 8/2005 | Van Emelen et al. |
| 2005/0197336 A1 | 9/2005 | Anandan et al. |
| 2005/0222414 A1 | 10/2005 | Van Emelen et al. |
| 2007/0135424 A1 | 6/2007 | Van Brandt et al. |
| 2008/0132459 A1 | 6/2008 | Moradei et al. |
| 2008/0255140 A1 | 10/2008 | Van Emelen |
| 2009/0005393 A1 | 1/2009 | Angibaud et al. |
| 2009/0018152 A1 | 1/2009 | Angibaud et al. |
| 2009/0018153 A1 | 1/2009 | Angibaud et al. |
| 2009/0023726 A1 | 1/2009 | Roux et al. |
| 2009/0036463 A1 | 2/2009 | Angibaud et al. |
| 2009/0042920 A1 | 2/2009 | Van Emelen et al. |
| 2009/0124646 A1 | 5/2009 | Verdonck et al. |
| 2009/0143401 A1 | 6/2009 | Marconnet-Decrane et al. |
| 2009/0170836 A1 | 7/2009 | Angibaud et al. |
| 2009/0170881 A1 | 7/2009 | Angibaud et al. |
| 2009/0221580 A1 | 9/2009 | Angibaud et al. |
| 2009/0227558 A1 | 9/2009 | Angibaud et al. |
| 2009/0270419 A1 | 10/2009 | Arts et al. |
| 2010/0009988 A1 | 1/2010 | Van Emelen |
| 2010/0048588 A1 | 2/2010 | Van Emelen et al. |
| 2010/0160321 A1 | 6/2010 | Ten Holte et al. |
| 2010/0222574 A1 | 9/2010 | Rombouts et al. |
| 2010/0234353 A1 | 9/2010 | Van Emelen et al. |
| 2010/0240639 A1 | 9/2010 | Van Emelen et al. |

FOREIGN PATENT DOCUMENTS

| | | |
|---|---|---|
| DE | 04228792 | 3/1994 |
| DE | 10233412 | 2/2004 |
| EP | 076530 | 12/1985 |
| EP | 0188095 | 3/1992 |
| EP | 0827742 | 3/1998 |
| EP | 1002795 | 5/2000 |
| EP | 0788360 | 5/2003 |
| EP | 1472216 | 11/2004 |
| EP | 1485353 | 12/2004 |
| EP | 1495002 | 1/2005 |
| EP | 1523470 | 4/2005 |
| EP | 1525199 | 4/2005 |
| EP | 1572626 | 9/2005 |
| EP | 1583736 | 10/2005 |
| EP | 1585735 | 10/2005 |
| EP | 1592667 | 11/2005 |
| EP | 1312609 | 12/2005 |
| EP | 1608628 | 12/2005 |
| EP | 1613622 | 1/2006 |
| EP | 1663953 | 6/2006 |
| EP | 1501508 | 2/2007 |
| EP | 1581484 | 7/2007 |
| EP | 1592665 | 7/2007 |
| EP | 1685094 | 8/2007 |
| EP | 1485354 | 5/2008 |
| EP | 1485365 | 5/2008 |
| EP | 1485348 | 6/2008 |
| EP | 1485378 | 6/2008 |
| EP | 1492534 | 6/2008 |
| EP | 1627880 | 10/2008 |
| EP | 1485364 | 3/2009 |
| EP | 1485370 | 3/2009 |
| EP | 1682538 | 5/2009 |
| EP | 1611088 | 6/2009 |
| EP | 1590340 | 4/2010 |
| EP | 1673349 | 6/2010 |
| EP | 1485099 | 7/2010 |
| ES | 2104509 | 10/1997 |
| GB | 0901749 | 7/1962 |
| GB | 1345872 | 2/1974 |
| WO | WO 94/25437 | 11/1994 |
| WO | WO 96/13266 | 5/1996 |
| WO | WO 97/18839 | 5/1997 |
| WO | WO 97/23216 | 7/1997 |
| WO | WO 98/05335 | 2/1998 |
| WO | WO 98/55449 | 12/1998 |
| WO | WO 99/50250 | 10/1999 |
| WO | WO 00/26203 | 5/2000 |
| WO | WO 00/27825 | 5/2000 |
| WO | WO 00/35855 | 6/2000 |
| WO | WO 00/43394 | 7/2000 |
| WO | WO 00/52001 | 9/2000 |
| WO | WO 00/69821 | * 11/2000 |
| WO | WO 00/71516 | 11/2000 |
| WO | WO 01/09134 | 2/2001 |
| WO | WO 01/38322 | 5/2001 |
| WO | WO 01/49688 | 7/2001 |
| WO | WO 01/70675 | 9/2001 |
| WO | WO 02/00651 | 1/2002 |
| WO | WO 02/18335 | 3/2002 |
| WO | WO 02/42271 | 5/2002 |
| WO | WO 03/000653 | 1/2003 |
| WO | WO 03/011851 | 2/2003 |
| WO | WO 03/016306 | 2/2003 |
| WO | WO 03/035855 | 5/2003 |
| WO | WO 03/066579 | 8/2003 |
| WO | WO 03/076395 | 9/2003 |
| WO | WO 03/076400 | 9/2003 |
| WO | WO 03/076401 | 9/2003 |
| WO | WO 03/076421 | 9/2003 |
| WO | WO 03/076422 | 9/2003 |
| WO | WO 03/076430 | 9/2003 |
| WO | WO 03/076438 | 9/2003 |
| WO | WO 03/082288 | 10/2003 |
| WO | WO 03/087057 | 10/2003 |
| WO | WO 03/092686 | 11/2003 |
| WO | WO 2004/009536 | 1/2004 |
| WO | WO 2004/013130 | 2/2004 |
| WO | WO 2004/056748 | 7/2004 |
| WO | WO 2004/063146 | 7/2004 |
| WO | WO 2004/063169 | 7/2004 |
| WO | WO 2004/065354 | 8/2004 |
| WO | WO 2004/069803 | 8/2004 |
| WO | WO 2004/069823 | 8/2004 |
| WO | WO 2004/071400 | 8/2004 |
| WO | WO 2004/072047 | 8/2004 |
| WO | WO 2004/082638 | 9/2004 |
| WO | WO 2004/087693 | 10/2004 |
| WO | WO 2004/092115 | 10/2004 |
| WO | WO 2005/028447 | 3/2005 |
| WO | WO 2005/030704 | 4/2005 |
| WO | WO 2005/030705 | 4/2005 |
| WO | WO 2005/040101 | 5/2005 |
| WO | WO 2005/040161 | 5/2005 |
| WO | WO 2005/075469 | 8/2005 |
| WO | WO 2005/086898 | 9/2005 |
| WO | WO 2005/092899 | 10/2005 |
| WO | WO 2006/010749 | 2/2006 |
| WO | WO 2006/010750 | 2/2006 |
| WO | WO 2006/122926 | 11/2006 |
| WO | WO 2006/136553 | 12/2006 |
| WO | WO 2007/016532 | 2/2007 |
| WO | WO 2007/048767 | 5/2007 |
| WO | WO 2007/082873 | 7/2007 |
| WO | WO 2007/082874 | 7/2007 |
| WO | WO 2007/082876 | 7/2007 |
| WO | WO 2007/082878 | 7/2007 |
| WO | WO 2007/082880 | 7/2007 |
| WO | WO 2007/082882 | 7/2007 |
| WO | WO 2008/031820 | 3/2008 |

OTHER PUBLICATIONS

U.S. Appl. No. 10/507,084: Non-Final Office Action, dated Jul. 22, 2008, 5 pages.

U.S. Appl. No. 10/507,084: Non-Final Office Action, dated Jun. 1, 2007, 7 pages.

U.S. Appl. No. 10/507,159: Non-Final Office Action, dated Jun. 25, 2009, 7 pages.

U.S. Appl. No. 10/507,271: Final Office Action, dated May 2, 2008, 5 pages.

U.S. Appl. No. 10/507,271: Non-Final Office Action, dated Jul. 25, 2007, 12 pages.

(56) References Cited

OTHER PUBLICATIONS

U.S. Appl. No. 10/507,708: Final Office Action, dated May 8, 2006, 11 pages.
U.S. Appl. No. 10/507,708: Non-Final Office Action, dated Nov. 23, 2005, 15 pages.
U.S. Appl. No. 10/507,784: Non-Final Office Action, dated Apr. 6, 2007, 13 pages.
U.S. Appl. No. 10/507,784: Non-Final Office Action, dated Feb. 13, 2008, 5 pages.
U.S. Appl. No. 10/507,784: Non-Final Office Action, dated Sep. 24, 2007, 5 pages.
U.S. Appl. No. 10/507,785: Non-Final Office Action, dated Jul. 19, 2007, 16 pages.
U.S. Appl. No. 10/507,785: Non-Final Office Action, dated May 13, 2008, 6 pages.
U.S. Appl. No. 10/507,788: Non-Final Office Action, dated Oct. 19, 2007, 17 pages.
U.S. Appl. No. 11/572,563: Advisory Action, dated Jun. 3, 2011, 2 pages.
U.S. Appl. No. 11/572,563: Final Office Action, dated Jul. 9, 2010, 8 pages.
U.S. Appl. No. 11/572,563: Final Office Action, dated Mar. 3, 2011, 5 pages.
U.S. Appl. No. 11/572,563: Non-Final Office Action, dated Sep. 29, 2009, 14 pages.
U.S. Appl. No. 11/626,215: Ex-Parte Quayle Action, dated Apr. 2, 2009, 6 pages.
U.S. Appl. No. 11/626,215: Non-Final Office Action, dated Jul. 9, 2008, 14 pages.
U.S. Appl. No. 11/668,906: Non-Final Office Action, dated Feb. 20, 2009, 8 pages.
U.S. Appl. No. 11/914,208: Non-Final Office Action, dated Mar. 10, 2011, 5 pages.
U.S. Appl. No. 11/914,208: Non-Final Office Action, dated Oct. 1, 2010, 10 pages.
U.S. Appl. No. 11/917,999: Final Office Action, dated Feb. 24, 2011, 15 pages.
U.S. Appl. No. 11/917,999: Non-Final Office Action, dated Sep. 15, 2010, 13 pages.
U.S. Appl. No. 11/926,759: Non-Final Office Action, dated May 13, 2009, 9 pages.
U.S. Appl. No. 12/090,771: Advisory Action, dated Dec. 2, 2009, 3 pages.
U.S. Appl. No. 12/090,771: Final Office Action, dated Aug. 24, 2009, 6 pages.
U.S. Appl. No. 12/090,771: Non-Final Office Action, dated Dec. 23, 2008, 11 pages.
U.S. Appl. No. 12/160,120: Non-Final Office Action, dated Sep. 30, 2009, 13 pages.
U.S. Appl. No. 12/160,124: Non-Final Office Action, dated Mar. 25, 2011, 12 pages.
U.S. Appl. No. 12/160,133: Non-Final Office Action, dated Sep. 29, 2009, 12 pages.
U.S. Appl. No. 12/160,140: Non-Final Office Action, dated Aug. 9, 2010, 6 pages.
U.S. Appl. No. 12/160,140: Non-Final Office Action, dated Sep. 30, 2009, 14 pages.
U.S. Appl. No. 12/160,156: Non-Final Office Action, dated Sep. 29, 2009, 13 pages.
U.S. Appl. No. 12/160,221: Non-Final Office Action, dated Jan. 19, 2010, 7 pages.
U.S. Appl. No. 12/233,977: Non-Final Office Action, dated Jun. 3, 2010, 6 pages.
U.S. Appl. No. 12/360,139: Final Office Action, dated Mar. 17, 2011, 8 pages.
U.S. Appl. No. 12/360,139: Non-Final Office Action, dated Aug. 19, 2010, 22 pages.
U.S. Appl. No. 12/372,801: Final Office Action, dated Nov. 29, 2010, 6 pages.
U.S. Appl. No. 12/372,801: Non-Final Office Action, dated Dec. 10, 2009, 7 pages.
U.S. Appl. No. 12/372,801: Non-Final Office Action, dated Jun. 10, 2010, 5 pages.
U.S. Appl. No. 12/539,682: Final Office Action, dated Feb. 1, 2011, 11 pages.
U.S. Appl. No. 12/539,682: Non-Final Office Action, dated Aug. 17, 2010, 8 pages.
U.S. Appl. No. 12/759,256: Non-Final Office Action, dated Jan. 7, 2011, 7 pages.
Acharya et al., "Rational Development of Histone Deacetylase Inhibitors as Anticancer Agents: A Review," *Molecular Pharmacology*, 2005; 68(4):917-932.
Angibaud et al., "Discovery of Pyrimidyl-5-Hydroxamic Acids as New Potent Histone Deacetylase Inhibitors," *European Journal of Medicinal Chemistry*, 2005; 40:597-606.
Archibald, et al., "Benzamidopiperidines 3. Carbocyclic Derivatives Related to Indoramin," Journal of Medicinal Chemistry, 1974, 17(7), 739-744.
Awada et al., "The Pipeline of New Anticancer Agents for Breast Cancer Treatment in 2003," Oncology Hematology, 2003, 48, 45-63.
Bali, et al., "A Combination of Histone Deacetylase Inhibitor LAQ 824 and the FLT-3 Kinase Inhibitor PKC412 is Highly Active Against Human AML Cells with Constitutively Active Mutant FLT-3 Tyrosine Kinase," Blood, 2003,102(11), 96a-97b.
Bali et al., "Inhibition of Histone Deacetylase 6 Acetylates and Disrupts the Chaperone Function of Heat Shock Protein 90," *Journal of Biological Chemistry*, 2005, 280(29):26729-26734.
Bali et al., "Mechanisms Underlying Hydroxamic Acid Analogue (HA) Histone Deacetylase (HDAC) Inhibitors (HDIs)-Induced Apoptosis: New Role of HDAC6 Inhibition, Acetylation and Inhibition of hsp90 and Depletion of Pro-Growth and ProSurvival Oncoproteins," Proceedings of the American Association for Cancer Research Annual Meetings, 2005, 46, #3268, 769-770.
Banker, et al., "Prodrugs," Modern Pharmaceuticals, Marcel Dekker, Inc., 3$^{rd}$ Ed. 1996, 596.
Bertino, et al., "Principles of Cancer," Cecil's Textbook of Medicine, 2000, 21$^{st}$ Ed., vol. 1, 1060-1074.
Birch et al., "N-Substituted (2, 3-Dihydro-1, 4-benzodioxin-2-yl)methylamine Derivatives as D2 Antagonists/5-HT1A Partial Agonists with Potential as Atypical Antipsychotic Agents," *J. Med. Chem.*, 1999; 42:3342-3355.
Blagosklonny et al., "Histone Deacetylase Inhibits all Induce P21 but Differentially Cause Tubulin Acetylation, Mitotic Arrest, and Cytotoxicity," *Molecular Cancer Therapeutics*, 2002; 1(11):937-941.
Calabresi P. and Chabner BA, "Section IX Chemotherapy of Neoplastic Diseases—Introduction," Goodman & Gilman's *The Pharmacological Basis of Therapeutics*, 10th ed., 2001, Hardman JG, Limbird LE, and Gilman AG, Eds, McGraw-Hill, New York 2001, 1381-1386 (1381, 1383-1385, 1388 provided).
Carter et al., "Chemotherapy of Cancer," Wiley (2$^{nd}$ Edition), 1981, 362-365.
Catley et al., "Novel Hydroxamic Acid-Derived HDAC Inhibitor LBH589 Potently Activates Intrinsic and Induces Tubulin Hyperacetylation in Multiple Myeloma," *Blood*, 2005; 106(11):Abstract 1578; p. 435A.
Chen et al., "A Short and General Approach to the Synthesis of Styryllactones: (+)-Goniodiol, its Acetates and β-Trifluoromethyl Derivative, (+)-7-*epi*-Goniodiol and (+)-9-Deoxygoniopypyrone," *Synlett*, 2002; 8:1265-1268.
Chou et al., "Chemotherapeutic Synergism, Potentiation and Antagonism," *Encyclopedia of Human Biology*, 1991; 2:371-379.
Chou et al., "Computerized Quantitation of Synergism and Antagonism of Taxol, Topotecan, and Cisplatin Against Human Teratocarcinoma Cell Growth: A Rational Approach to Clinical Protocol Design," *J. Natl. Cancer Inst.*, 1994; 86(20):1517-1524.
Chou et al., "Quantitative Analysis of Dose-Effect Relationships: The Combined Effects of Multiple Drugs or Enzyme Inhibitors," *Adv. Enzyme Regul.*, 1984; 22: 27-55.
Chou et al., "The Median-Effect Principle and the Combination Index for Quantitation of Synergism and Antagonism," *Synergism and Antagonism in Chemotherapy*, 1991; pp. 60-103.

(56) References Cited

OTHER PUBLICATIONS

Dankwardt, et al., "Solid Phase Synthesis of Aryl and Benzylpiperazines and their Applications in Combinatorial Chemistry," *Tetrahedron Letters*, 1995; 36(28):4923-4926.
Dermer et al., "Another Anniversary for the War on Cancer," *BioTechnology*, 1994; 12:320.
Dorwald, Side Reactions In organic Synthesis, 2005, Wiley: VCH, Weinheim p. IX of Preface.
Finney, D.J., "Probit Analyses,—A Statietical Treatment of the Sigmold Response Curve," Graded Responses, Cambridge University Press, 1962: 2nd Ed. Chapter 10.
Finnin, M., et al., "Structures of a Histone Deacetylase Homologue Bound to the TSA and SAHA Inhibitors," Nature, 401, 188-193, (1999).
Foks, H., et al., "Investigations on Pyrazine Derivatives Part II. Synthesis and Tuberculostatic Action of Some 6-Alkylaminopyrazine-2-Carboxylic Acids," Dissert. Pharm. Pharmacol. 24, 1972, 577-583.
Foks, H., et al., "Studies on Pyrazine Derivatives Part X. Synthesis and Tuberculostatic Activity of some 6-Cyanolamino-6-Imidazolyl- and Triazolypyrazine-2-carboxylic Acids Derivatives," Po.J. Pharmacol. Pharm., 30, 1978, 105-111.
Freshney et al., "Culture of Animal Cells, A Manual of Basic Technique," Alan R Liss, Inc. 1983 New York, p. 1-6.
George et al., "Combination of Histone Deacetylase Inhibitor LBH589 and the hsp90 Inhibitor 17-AAG is Highly Active Against Human CML-BC Cells and AML Cells with Activating Mutation of FLT-3," *Blood*, 2005; 105(4):1768-1776.
Glaser, "HDAC Inhibitors: Clinical Update and Mechanism-Based Potential," *Biochemical Pharmacology*, 2007; 74(5):659-671.
Golub et al., "Molecular Classification of Cancer: Class Discovery and Class Prediction by Gene Expression Monitoring," *Science*, 1999; 286:531-537.
Gorrod, J., et al., "The Metabolism of N-Ethyl-N-Methylaniline by Rabbit Liver Microsomes: The Measurement of Metabolites by Gas-Liquid Chromatography," Xenobiotica, 5, 8, 1975, 453-463.
Gura, "Systems for Identifying New Drugs Are Often Faulty," Cancer Models, Science, vol. 278, No. 5340, 1041-1042, Nov. 1997.
Hideshima et al., "Small-Molecule Inhibition of Proteasome and Aggresome Function Induces Synergistic Antitumor Activity in Multiple Myeloma," *PNAS*, 2005; 102(24):8567-8572.
Horton et al., "Bortezomib Interactions with Chemotherapy Agents in Acute Leukemia In Vitro," *Cancer Chemotherapy and Pharmacology*, 2006; 58(1):13-23.
*Internal Medicine*, 4th Edition, Editor-in-Chief Jay Stein, Chapters 71-72, pp. 699-715, (1994).
International Search Report from PCT/EP03/02510 dated May 22, 2003, 2 pages.
International Search Report from PCT/EP03/02511 dated May 22, 2003, 2 pages.
International Search Report from PCT/EP03/02512 dated Jun. 30, 2003, 4 pages.
International Search Report from PCT/EP03/02513 dated May 22, 2003, 2 pages.
International Search Report from PCT/EP03/02514 dated Aug. 13, 2003, 4 pages.
International Search Report from PCT/EP03/02515 dated Aug. 18, 2008, 5 pages.
International Search Report from PCP/EP03/02516 dated Aug. 13, 2003, 3 pages.
International Search Report from PCT/EP03/02517 dated May 22, 2003, 2 pages.
International Searoh Report from PCT/EP05/53611 dated Jan. 17, 2006, 4 pages.
International Search Report from PCP/EP05/53612 dated Jul. 10, 2005, 3 pages.
International Search Report from PCT/EP06/62324 dated Aug. 16, 2006, 4 pages.
International Search Report from PCP/EP06/63351 dated Aug. 11, 2006, 2 pages.
International Search Report from PCT/EP06/67656 dated Feb. 6, 2007, 4 pages.
International Search Report from PCT/EP07/50370 dated Mar. 14, 2007, 3 pages.
International Search Report from PCT/EP07/50371 dated May 8, 2007, 4 pages.
International Search Report from PCT/EP07/50374 dated Mar. 12, 2007, 4 pages.
International Search Report from PCT/EP07/50376 dated Mar. 28, 2007, 2 pages.
International Search Report from PCT/EP07/50379 dated May 8, 2007, 3 pages.
International Search Report from PCT/EP07/50381 dated Apr. 4, 2007, 2 pages.
International Search Report from PCT/EP07/59523 dated Mar. 20, 2008, 6 pages.
Irikura et al., "Absorption, Excretion, and Metabolism of 1-(p-aminobenzoyl)-4-(3, 4, 5-trimethoxybenzamido)piperidine (KU-55)," *Pharmacometrics*, 1973; 7(7):985-990. (With English-language Abstract).
Johnson et al., "Relationships Between Drug Activity in NCI Preclinical in vitro and in vivo Models and Early Clinical Trials," British Journal of Cancer, 2001, 64, 10, 1424-1431.
Khadikar, et al., CAPLUS Abstract 128:265724, 1998.
Khuthier, et al., "Studies of Tertiary Amine Oxides. 9. Thermal Rearrangement of 1-(4-Substituted-phenyl)piperdine N-Oxides to the Corresponding N-Hydroximes," J. Org. Chem. vol. 52, 1987, 1710-1713.
Kristeleit et al., "Histone Modification Enzymes: Novel Targets for Cancer Drugs," *Expert Opin. Emerg. Drugs*, 2004; 91(1):135-154.
Lentzsch et al., "Combination of Proteasome Inhibitor PS 341 with Histone Acetylase Inhibitor (HDAC) PXD 101 Shows Superior Anti-Myeloma Activity and Inhibits Osteoclastogenesis," *Blood Poster Session*, 2005; 106(Abstract 2488):p. 1.
Mai et al., Histone Deacetylation in Epigenetics: an Attractive Target for Anticancer Therapy, *Medicinal Research Reviews*, 2005; 25(3):261-309.
Marks, P., et al., "Histone Deacetylases and Cancer: Causes and Therapies," Reviews: Cancer, vol. 1, 2001, 194-2001.
Mitsiades et al., Transcriptional Signature of Histone Deacetylase Inhibition in Multiple Myeloma: Biological and Clinical Implications, *PNAS*, 2004; 101(2):540-545.
Monneret, "Histone Deacetylase Inhibitors," *European Journal of Medicinal Chemistry*, 2004; 40:1-13.
Mosmann, T., et al., "Rapid Colorimetric Assay for Cellular Growth and Survival: Application to Proliferation and Cytotoxicity Assays," Journal of Immunological Methods, vol. 65, 1983, 55-63.
Nawrocki et al., "Aggresome Disruption: A Novel Strategy to Enhance Bortezomib-Induced Apoptosis in Pancreatic Cancer Cells," *Cancer Research*, 2006; 66(7):3773-3781.
Pan P.C. et al., "Soluble Polymer-Supported Synthesis of Arylpiperazines," *Tetrahadron Letters*, 1998; 39:9505-9508.
Pasternak et al., "Potent, orally bioavailable somoatostatin agonists; good absorption achieved by urea backbone cyclization," *Bioorganic and Medicinal Chemistry Letters 9*, 1999; 9:491-496.
Patani et al., "Bioisosterism: A Rational Approach in Drug Design," *Chem. Rev.*, 1996; 96:3147-3176.
Pei Xin-Yan et al., "Synergistic Induction of Oxidative Injury and Apoptosis in Human Multiple Myeloma Cells by the Proteasome Inhibitor Bortezomib and Histone Deacetylase Inhibitors," *Clinical Cancer Research*, 2004; 10:3839-3852.
Sausville et al., "Contributions of Human Tumor Xenografts to Anticancer Drug Development," *American Association for Cancer Research*, 2006; 66(7):3351-3354.
Simone, J.V., "Oncology: Introduction," *Cecil's Textbook of Medicine*, 1996; 20th Edition, vol. 1:1004-1010.
Sternson et al., "Synthesis of 7200 Small Molecules Based on a Substructural Analysis of the Histone Deacetylase Inhibitors Trichostatin and Trapoxin," *Organic Letters*, 2001; 3(26):4239-4242.

(56) References Cited

OTHER PUBLICATIONS

Sutheesophon et al., "Histona Deacetylase Inhibitor Despsipeptides (FK228) Induces Apoptosis in Leukemic Cells by Facilitating Mitochondrial Translocation of Bax, Which is Enhanced by the Proteasome Inhibitor Bortezomid," *ACTA Haematologica*, 2006; 115:78-90.

Takai et al., "Human Ovarian Carcinoma Cells: Histone Deacetylase Inhibitors Exhibit Antiproliferative Activity and Potently Induce Apoptosis," *American Cancer Society*, 2004; 101(12):2760-2770.

Taylor et al., CAPLUS Abstract 55:33107 (1961).

Van Emelen et al., "Discovery of a Novel Class of Aromatic Hydroxamic Acids as Potent HDAC Inhibitors," *AACR-NCI_Eortc International Conference on Molecular Targets and Cancer Therapeutics*, 2003, XP009095813.

Walsh, D., et al., "Synthesis and Antiallergy Activity of N-[2-(Dimethylamino)ethyl]-4-Aryl-1-piperazinecarboxamide Derivatives," J. Med. Chemistry, vol. 33, 1990, 2028-2032.

Wolff, Burger's Medicinal Chemistry, 5th Ed. Part 1, pp. 975-977 (1995).

Yokoyama et al., CAPLUS Abstract 105:208919 (1986).

Yokoyama et al., CAPLUS Abstract 105:226622 (1986).

Yu et al., "The Proteasome Inhibitor Bortezomib Interacts Synergistically with Histone Deacetylase Inhibitors to Induce Apoptosis in Bcr/Abl+ Cells Sensitive and Resistant to STI571," *Blood*, 2003; 102:3765-3774.

\* cited by examiner

INHIBITORS OF HISTONE DEACETYLASE

CROSS REFERENCE TO RELATED APPLICATIONS

This application is a divisional of U.S. application Ser. No. 12/560,657, filed Sep. 16, 2009, which is a divisional of U.S. application Ser. No. 10/507,785, filed Sep. 13, 2004, now U.S. Pat. No. 7,615,553, which in turn is a National Stage application under 35 U.S.C. §371 of International Application No. PCT/EP03/02515 filed Mar. 11, 2003, which claims the benefit of U.S. Provisional Application No. 60/363,799, filed 13 Mar. 2002.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

In all eukaryotic cells, genomic DNA in chromatine associates with histones to form nucleosomes. Each nucleosome consists of a protein octamer made up of two copies of each histones H2A, H2B, H3 and H4. DNA winds around this protein core, with the basic amino acids of the histones interacting with the negatively charged phosphate groups of the DNA. The most common posttranslational modification of these core histones is the reversible acetylation of the E-amino groups of conserved, highly basic N-terminal lysine residues. The steady state of histone acetylation is established by the dynamic equilibrium between competing histone acetyltransferase(s) and histone deacetylase(s) herein referred to as "HDAC". Histone acetylation and deacetylation has long been linked to transcriptional control. The recent cloning of the genes encoding different histone acetyltransferases and histone deacetylases provided a possible explanation for the relationship between histone acetylation and transcriptional control. The reversible acetylation of histones can result in chromatin remodelling and as such act as a control mechanism for gene transcription. In general, hyperacetylation of histones facilitates gene expression, whereas histone deacetylation is correlated with transcriptional repression. Histone acetyltransferases were shown to act as transcriptional coactivators, whereas histone deacetylases were found to belong to transcriptional repression pathways.

The dynamic equilibrium between histone acetylation and deacetylation is essential for normal cell growth. Inhibition of histone deacetylase results in cell cycle arrest, cellular differentiation, apoptosis and reversal of the transformed phenotype. Therefore HDAC inhibitors can have great therapeutic potential in the treatment of cell proliferative diseases or conditions (Marks et al., Nature Reviews: Cancer 1: 194-202, 2001)

The study of inhibitors of histone deacetylases (HDAC) indicates that indeed these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 Mar. 1998).

Patent application WO01/38322 published on May 31, 2001 discloses amongst others inhibitors of histone deacetylase of general formula Cy-L$^1$-Ar—Y$^1$—C(O)—NH—Z, providing compositions and methods for treating cell proliferative diseases and conditions.

Patent application WO01/70675 published on 27 Sep. 2001 discloses inhibitors of histone deacetylase of formula Cy-X—Y$^1$—W and Cy-S(O)$_2$—NH—Y$^3$—W and further provides compositions and methods for treating cell proliferative diseases and conditions.

The problem to be solved is to provide histone deacetylase inhibitors with high enzymatic activity and also show advantageous properties such as cellular activity and increased bioavailability, preferably oral bioavailability, and have little or no side effects.

The novel compounds of the present invention solve the above described problem. The compounds differ from the prior art in structure.

The compounds of the present invention show excellent in-vitro histone deacetylase inhibiting enzymatic activity. The present compounds have advantageous properties with regard to cellular activity and specific properties with regard to inhibition of cell cycle progression at both G1 and G2 checkpoints (p21 induction capacity). The compounds of the present invention show good metabolic stability and high bioavailability and more particular they show oral bioavailability.

This invention concerns compounds of formula (I)

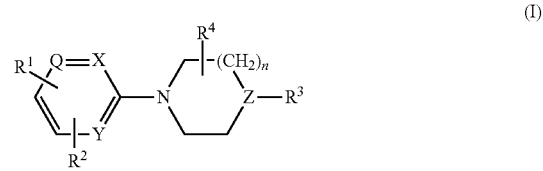

the N-oxide forms, the pharmaceutically acceptable addition salts and the stereo-chemically isomeric forms thereof, wherein n is 0, 1, 2 or 3 and when n is 0 then a direct bond is intended;

each Q is nitrogen or

each X is nitrogen or

each Y is nitrogen or

each Z is nitrogen or

R¹ is —C(O)NR⁵R⁶, —N(H)C(O)R⁷, —C(O)—C$_{1-6}$alkanediylSR⁷, —NR⁸C(O)N(OH)R⁷, —NR⁸C(O)C$_{1-6}$alkanediylSR⁷, —NR⁸C(O)C=N(OH)R⁷ or another Zn-chelating-group wherein R⁵ and R⁶ are each independently selected from hydrogen, hydroxy, C$_{1-6}$alkyl, hydroxyC$_{1-6}$alkyl, aminoC$_{1-6}$alkyl or aminoaryl;

R⁷ is independently selected from hydrogen, C$_{1-6}$alkyl, C$_{1-6}$alkylcarbonyl, arylC$_{1-6}$alkyl, C$_{1-6}$alkylpyrazinyl, pyridinone, pyrrolidinone or methyl imidazolyl;

R⁸ is independently selected from hydrogen or C$_{1-6}$alkyl;

R² is hydrogen, halo, hydroxy, amino, nitro, C$_{1-6}$alkyl, C$_{1-6}$alkyloxy, trifluoromethyl, di(C$_{1-6}$alkyl)amino, hydroxyamino or naphtalenylsulfonylpyrazinyl;

R³ is hydrogen, C$_{1-6}$alkyl, arylC$_{2-6}$alkenediyl, furanylcarbonyl, naphtalenylcarbonyl, —C(O)phenylR⁹, C$_{1-6}$alkylaminocarbonyl, aminosulfonyl, arylaminosulfonyl, aminosulfonylamino, di(C$_{1-6}$alkyl)aminosulfonylamino, arylaminosulfonylamino, aminosulfonylaminoC$_{1-6}$alkyl, di(C$_{1-6}$alkyl)aminosulfonylaminoC$_{1-6}$alkyl, arylaminosulfonylaminoC$_{1-6}$alkyl, di(C$_{1-6}$alkyl)aminoC$_{1-6}$alkyl, C$_{1-12}$alkylsulfonyl, di(C$_{1-6}$alkyl)aminosulfonyl, trihaloC$_{1-6}$alkylsulfonyl, di(aryl)C$_{1-6}$alkylcarbonyl, thiophenylC$_{1-6}$alkylcarbonyl, pyridinylcarbonyl or arylC$_{1-6}$alkylcarbonyl wherein each R⁹ is independently selected from phenyl; phenyl substituted with one, two or three substituents independently selected from halo, amino, C$_{1-6}$alkyl, C$_{1-6}$alkyloxy, hydroxyC$_{1-4}$alkyl, hydroxyC$_{1-4}$alkyloxy, aminoC$_{1-4}$alkyloxy, di(C$_{1-4}$alkyl)aminoC$_{1-4}$alkyloxy, di(C$_{1-6}$alkyl)aminoC$_{1-6}$alkyl, di(C$_{1-6}$alkyl)aminoC$_{1-6}$alkyl(C$_{1-6}$alkyl)aminoC$_{1-6}$alkyl, hydroxyC$_{1-4}$alkylpiperazinylC$_{1-4}$alkyl, C$_{1-4}$alkyloxypiperidinylC$_{1-4}$alkyl, hydroxyC$_{1-4}$alkyloxyC$_{1-4}$alkylpiperazinyl, C$_{1-4}$alkylpiperazinylC$_{1-4}$alkyl, di(hydroxyC$_{1-4}$alkyl)aminoC$_{1-4}$alkyl, pyrrolidinylC$_{1-4}$alkyloxy, morpholinylC$_{1-4}$alkyloxy, or morpholinylC$_{1-4}$alkyl; thiophenyl; or thiophenyl substituted with di(C$_{1-4}$alkyl)aminoC$_{1-4}$alkyloxy, di(C$_{1-6}$alkyl)aminoC$_{1-6}$alkyl, di(C$_{1-6}$alkyl)aminoC$_{1-6}$alkyl(C$_{1-6}$alkyl)aminoC$_{1-6}$alkyl, pyrrolidinylC$_{1-4}$alkyloxy, C$_{1-4}$alkylpiperazinylC$_{1-4}$alkyl, di(hydroxyC$_{1-4}$alkyl)aminoC$_{1-4}$alkyl or morpholinylC$_{1-4}$alkyloxy.

R⁴ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;

when R³ and R⁴ are present on the same carbon atom, R³ and R⁴ together may form a bivalent radical of formula

 (a-1)

wherein R¹⁰ is hydrogen or aryl;

when R³ and R⁴ are present on adjacent carbon atoms, R³ and R⁴ together may form a bivalent radical of formula

 (b-1);

aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; C$_{1-6}$alkyl includes C$_{1-4}$alkyl and the higher homologues thereof having 5 to 6 carbon atoms such as, for example, pentyl, 2-methylbutyl, hexyl, 2-methylpentyl and the like; C$_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihaloC$_{1-6}$alkyl defines C$_{1-6}$alkyl containing three identical or different halo substituents for example trifluoromethyl; C$_{2-6}$alkenediyl defines bivalent straight and branched chain hydrocarbon radicals containing one double bond and having from 2 to 6 carbon atoms such as, for example, ethenediyl, 2-propenediyl, 3-butenediyl, 2-pentenediyl, 3-pentenediyl, 3-methyl-2-butenediyl, and the like; and aminoaryl defines aryl substituted with amino.

The term "another Zn-chelating group" refers to a group, which is capable of interacting with a Zn-ion, which can be present at an enzymatic binding site.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures, which are not interchangeable, which the compounds of formula (I) may possess. Unless otherwise mentioned or indicated, the chemical designation of a compound encompasses the mixture of all possible stereochemically isomeric forms, which said compound might possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source.

A first group of interesting compounds consists of those compounds of formula (I) wherein one or more of the following restrictions apply:
a) n is 0 or 1;
b) each Q is

c) $R^1$ is —C(O)NH(OH) or —NHC(O)$C_{1-6}$alkanediylSH;
d) $R^2$ is hydrogen or nitro;
e) $R^3$ is $C_{1-6}$alkyl, aryl$C_{2-6}$alkenediyl, furanylcarbonyl, naphtalenylcarbonyl, $C_{1-6}$alkylaminocarbonyl, aminosulfonyl, di($C_{1-6}$alkyl)aminosulfonylamino$C_{1-6}$alkyl, di($C_{1-6}$alkyl)amino$C_{1-6}$alkyl, $C_{1-12}$alkylsulfonyl, di($C_{1-6}$alkyl)aminosulfonyl, trihalo$C_{1-6}$alkylsulfonyl, di(aryl)$C_{1-6}$alkylcarbonyl, thiophenyl$C_{1-6}$alkylcarbonyl, pyridinylcarbonyl or aryl$C_{1-6}$alkylcarbonyl;
f) $R^4$ is hydrogen;
g) when $R^3$ and $R^4$ are present on the same carbon atom $R^3$ and $R^4$ together may form a bivalent radical of formula (a-1) wherein $R^{10}$ is aryl;
h) when $R^3$ and $R^4$ are present on adjacent carbon atoms $R^3$ and $R^4$ together may form a bivalent radical of formula (b-1).

A second group of interesting compounds consists of those compounds of formula (I) wherein one or more of the following restrictions apply:
a) n is 1;
b) each Q is

c) each Z is nitrogen;
d) $R^1$ is —C(O)NH(OH);
e) $R^2$ is hydrogen;
f) $R^3$ is naphtalenylcarbonyl, $C_{1-12}$alkylsulfonyl or di(aryl)$C_{1-6}$alkylcarbonyl;
g) $R^4$ is hydrogen.

A third group of interesting compounds consists of those compounds of formula (I) wherein $R^2$ is hydrogen.

A fourth group of interesting compounds consists of those compounds of formula (I) wherein $R^1$ is —C(O)NH(OH).

A fifth group of interesting compounds consists of those compounds of formula (I) wherein $R^2$ is hydrogen and $R^1$ is —C(O)NH(OH).

A sixth group of interesting compounds consists of those compounds of formula (I) wherein one or more of the following restrictions apply;
a) $R^1$ is —C(O)N$R^5R^6$, —C(O)—$C_{1-6}$alkanediylS$R^7$, —N$R^8$C(O)N(OH)$R^7$, —N$R^8$C(O)$C_{1-6}$alkanediylS$R^7$, —N$R^8$C(O)C=N(OH)$R^7$ or another Zn-chelating-group wherein $R^5$ and $R^6$ are each independently selected from hydrogen, hydroxy, hydroxy$C_{1-6}$alkyl or amino$C_{1-6}$alkyl;
b) $R^2$ is hydrogen, halo, hydroxy, amino, nitro, $C_{1-6}$alkyl, $C_{1-6}$alkyloxy, trifluoromethyl or di($C_{1-6}$alkyl)amino;
c) $R^3$ is hydrogen, $C_{1-6}$alkyl, aryl$C_{2-6}$alkenediyl, furanylcarbonyl, naphtalenylcarbonyl, —C(O)phenyl$R^9$, $C_{1-6}$alkylaminocarbonyl, aminosulfonyl, arylaminosulfonyl, aminosulfonylamino, di($C_{1-6}$alkyl)aminosulfonylamino, di($C_{1-6}$alkyl)amino$C_{1-6}$alkyl, $C_{1-12}$alkylsulfonyl, di($C_{1-6}$alkyl)aminosulfonyl or pyridinylcarbonyl wherein each $R^9$ is independently selected from phenyl; phenyl substituted with one, two or three substituents independently selected from halo, $C_{1-6}$alkyl, $C_{1-6}$alkyloxy; or thiophenyl;
d) $R^4$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl.

A group of preferred compounds consists of those compounds of formula (I) wherein
$R^1$ is —C(O)N$R^5R^6$, —C(O)—$C_{1-6}$alkanediylS$R^7$, —N$R^8$C(O)N(OH)$R^7$, —N$R^8$C(O)$C_{1-6}$alkanediylS$R^7$, —N$R^8$C(O)C=N(OH)$R^7$ or another Zn-chelating-group wherein $R^5$ and $R^6$ are each independently selected from hydrogen, hydroxy, hydroxy$C_{1-6}$alkyl or amino$C_{1-6}$alkyl;
$R^2$ is hydrogen, halo, hydroxy, amino, nitro, $C_{1-6}$alkyl, $C_{1-6}$alkyloxy, trifluoromethyl or di($C_{1-6}$alkyl)amino;
$R^3$ is hydrogen, $C_{1-6}$alkyl, aryl$C_{2-6}$alkenediyl, furanylcarbonyl, naphtalenylcarbonyl, —C(O)phenyl$R^9$, $C_{1-6}$alkylaminocarbonyl, aminosulfonyl, arylaminosulfonyl, aminosulfonylamino, di($C_{1-6}$alkyl)aminosulfonylamino, di($C_{1-6}$alkyl)amino$C_{1-6}$alkyl, $C_{1-12}$alkylsulfonyl, di($C_{1-6}$alkyl)aminosulfonyl or pyridinylcarbonyl wherein each $R^9$ is independently selected from phenyl; phenyl substituted with one, two or three substituents independently selected from halo, $C_{1-6}$alkyloxy; or thiophenyl; and $R^4$ is hydrogen, hydroxy, amino, hydroxy$C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl.

A further group of preferred compounds consists of those compounds of formula (I)
  wherein n is 0 or 1; each Q is

$R^1$ is —C(O)NH(OH) or —NHC(O)$C_{1-6}$alkanediylSH; $R^2$ is hydrogen or nitro; $R^3$ is $C_{1-6}$alkyl, aryl$C_{2-6}$alkenediyl, furanylcarbonyl, naphtalenylcarbonyl, $C_{1-6}$alkylaminocarbonyl, aminosulfonyl, di($C_{1-6}$alkyl)aminosulfonylamino$C_{1-6}$alkyl, di($C_{1-6}$alkyl)amino$C_{1-6}$alkyl, $C_{1-12}$alkylsulfonyl, di($C_{1-6}$alkyl)aminosulfonyl, trihalo$C_{1-6}$alkylsulfonyl, di(aryl)$C_{1-6}$alkylcarbonyl, thiophenyl$C_{1-6}$alkylcarbonyl, pyridinylcarbonyl or aryl$C_{1-6}$alkylcarbonyl; $R^4$ is hydrogen; when $R^3$ and $R^4$ are present on the same carbon atom $R^3$ and $R^4$ together may form a bivalent radical of formula (a-1) wherein $R^{10}$ is aryl; or when $R^3$ and $R^4$ are present on adjacent carbon atoms $R^3$ and $R^4$ together may form a bivalent radical of formula (b-1).

A group of more preferred compounds consists of those compounds of formula (I)
  wherein n is 1; each Q is

each Z is nitrogen; W is —C(O)NH(OH); $R^2$ is hydrogen; $R^3$ is naphtalenylcarbonyl, $C_{1-12}$alkylsulfonyl or di(aryl)$C_{1-6}$alkylcarbonyl; and $R^4$ is hydrogen.

Most preferred compounds are compounds No. 18, No. 5 and No. 24.

Co. No. 18

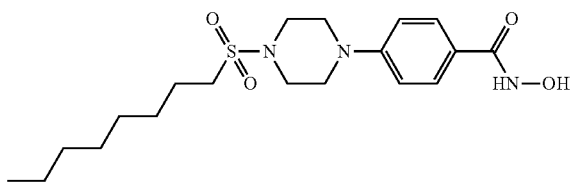

Co. No. 5

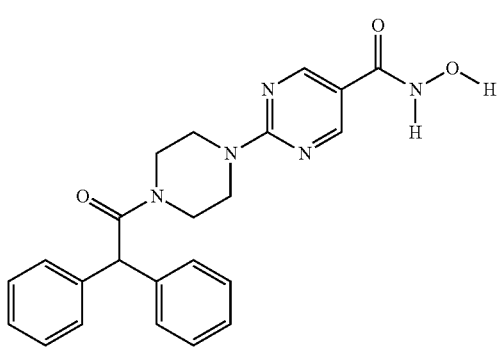

Co. No. 24

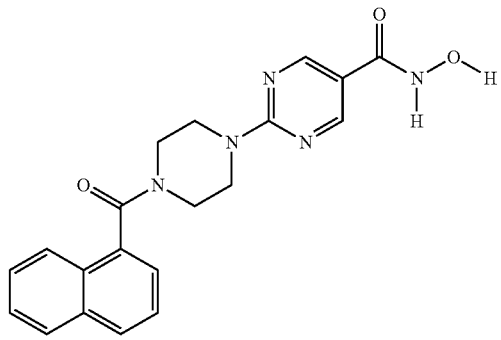

The compounds of formula (I) and their pharmaceutically acceptable salts and N-oxides and stereochemically isomeric forms thereof may be prepared in conventional manner.

A general synthesis route is encompassed as example:

a) Hydroxamic acids of formula (I) wherein $R^1$ is —C(O)NH (OH), said compounds being referred to as compounds of formula (I-a), may be prepared by reacting an intermediate of formula (II) with an appropriate acid, such as for example, trifluoro acetic acid. Said reaction is performed in an appropriate solvent, such as, for example, methanol.

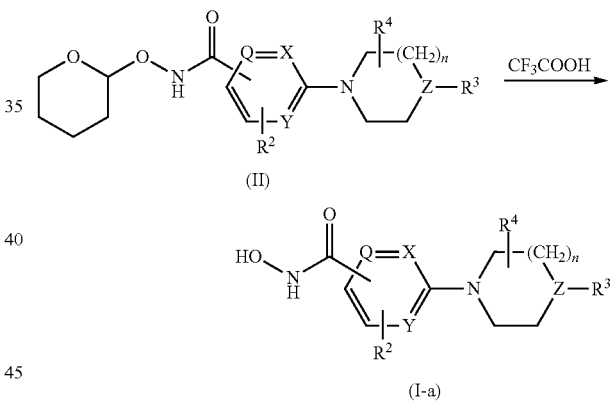

b) intermediates of formula (II) may be prepared by reacting an intermediate of formula (III) with an intermediate of formula (IV) in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in a suitable solvent such as a mixture of DCM and THF.

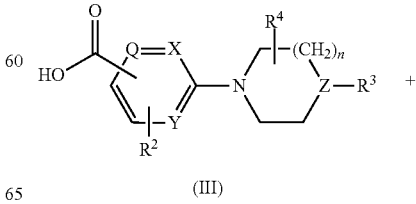

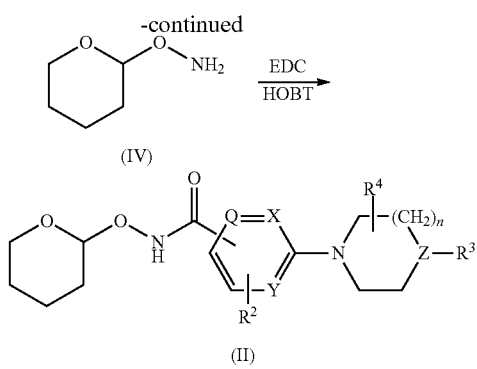

(IV)

(II)

c) intermediates of formula (III) may be prepared by reacting an intermediate of formula (V) with an appropriate base such as NaOH in the presence of a suitable solvent such as ethanol.

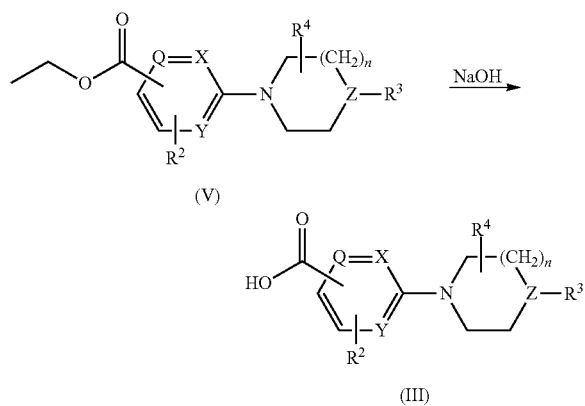

(V)

(III)

The compounds of formula (I) can also conveniently be prepared using solid phase synthesis techniques. In general, solid phase synthesis involves reacting an intermediate in a synthesis with a polymer support. This polymer-supported intermediate can then be carried on through a number of synthesis steps. After each step, filtering the resin and washing it numerous times with various solvents remove impurities. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry is described in for example "The Combinatorial Index" (B. Bunin, Academic Press) and Novabiochem's 1999 Catalogue & Peptide Synthesis Handbook (Novabiochem AG, Switzerland) both incorporated herein by reference.

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:
  a) the sensitisation of tumours to radiotherapy by administering the compound according to the invention before, during or after irradiation of the tumour for treating cancer;
  b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;
  c) inhibiting smooth muscle cell proliferation including vascular proliferative disorders, atherosclerosis and restenosis;
  d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia greata, scleroderma, exanthema, eczema, dermatomyositis, acne, diabetes, systemic lupus erythematosis, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating a cardiac dysfunction;
h) inhibiting immunosuppressive conditions such as the treatment of HIV infections;
i) treating renal dysfunction;
j) suppressing endocrine disorders;
k) inhibiting dysfunction of gluconeogenesis;
l) treating a neuropathology for example Parkinson's disease or a neuropathology that results in a cognitive disorder, for example, Alzheimer's disease or polyglutamine related neuronal diseases;
m) inhibiting a neuromuscular pathology, for example, amylotrophic lateral sclerosis;
n) treating spinal muscular atrophy;
o) treating other pathologic conditions amenable to treatment by potentiating expression of a gene;
p) enhancing gene therapy.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.05 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;
taxane compounds for example paclitaxel or docetaxel;
topoisomerase I inhibitors such as camptothecin compounds for example irinotecan or topotecan;
topoisomerase II inhibitors such as anti-tumour podophyllotoxin derivatives for example etoposide or teniposide;
anti-tumour vinca alkaloids for example vinblastine, vincristine or vinorelbine;
anti-tumour nucleoside derivatives for example 5-fluorouracil, gemcitabine or capecitabine;
alkylating agents such as nitrogen mustard or nitrosourea for example cyclophosphamide, chlorambucil, carmustine or lomustine;

anti-tumour anthracycline derivatives for example daunorubicin, doxorubicin, idarubicin or mitoxantrone;

HER2 antibodies for example trastuzumab;

estrogen receptor antagonists or selective estrogen receptor modulators for example tamoxifen, toremifene, droloxifene, faslodex or raloxifene;

aromatase inhibitors such as exemestane, anastrozole, letrazole and vorozole;

differentiating agents such as retinoids, vitamin D and retinoic acid metabolism blocking agents (RAMBA) for example accutane;

DNA methyl transferase inhibitors for example azacytidine;

kinase inhibitors for example flavoperidol, imatinib mesylate or gefitinib;

farnesyltransferase inhibitors; or other HDAC inhibitors.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived from extracts from certain species of yew (*Taxus*) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumor *vinca* alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis)

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:

short-chain fatty acids for example butyrate, 4-phenylbutyrate or valproic acid;

hydroxamic acids for example suberoylanilide hydroxamic acid (SAHA), biaryl hydroxamate A-161906, bicyclic aryl-N-hydroxycarboxamides, pyroxamide, CG-1521, PXD-101, sulfonamide hydroxamic acid, LAQ-824, trichostatin A (TSA), oxamflatin, scriptaid, m-carboxy cinnamic acid bishydroxamic acid, or trapoxin-hydroxamic acid analogue;

cyclic tetrapeptides for example trapoxin, apidicin or depsipeptide;

benzamides for example MS-275 or CI-994, or depudecin.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination according to the invention of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter $(mg/m^2)$ of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter $(mg/m^2)$ of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter $(mg/m^2)$ of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumor podophyllotoxin derivative is advantageously administered in a dosage of 30 to 300 mg per square meter $(mg/m^2)$ of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumor vinca alkaloid is advantageously administered in a dosage of 2 to 30 mg per square meter $(mg/m^2)$ of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumor nucleoside derivative is advantageously administered in a dosage of 200 to 2500 mg per square meter $(mg/m^2)$ of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter $(mg/m^2)$ of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumor anthracycline derivative is advantageously administered in a dosage of 10 to 75 mg per square meter $(mg/m^2)$ of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

Trastuzumab is advantageously administered in a dosage of 1 to 5 mg per square meter $(mg/m^2)$ of body surface area, particularly 2 to 4 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

Experimental Part

The following examples are provided for purposes of illustration.

"BSA" means bovine serum albumine, "DCM" means dichloromethane, "DIEM" means diisopropylethylamine, "DMF" means dimethylformamide, "DMSO" means dimethylsulfoxide, "EtOAc" means ethyl acetate, "Fmoc" means fluorenylmethoxycarbonyl, "Hepes" means 4-(-2-hydroxyethyl)-1-piperazine-ethanesulfonic acid, "HOBT" means 1-hydroxy-1H-benzotriazole, "MeOH" means methanol, "PyBop" means benzotriazole-1-yl-oxy-tris-pyrrolidino-phosphonium hexafluorophosphate, "PyBrOP" means bromo-tris-pyrrolidino-phosphonium hexafluorophosphate, "TEA" means triethylamine, "TFA" means trifluoroacetic acid "THF" means tetrahydrofuran, Extrelut™ is a product of Merck KgaA, Darmstadt, Germany, and is a short column comprising diatomaceous earth.

A. PREPARATION OF THE INTERMEDIATES

Example A1 a) Preparation of intermediate 1

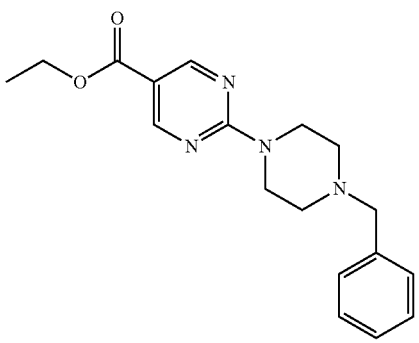

A solution of 1-(phenylmethyl)-piperazine (0.068 mol) in acetonitrile p.a. (135 ml) was added gradually to a solution of potassium carbonate (0.18 mol) and 2-(methylsulfonyl)-5-pyrimidinecarboxylic acid, ethyl ester (0.082 mol) in acetonitrile p.a. (135 ml) and the reaction mixture was stirred for 45 min at room temperature. Then, the reaction mixture was stood overnight. DCM (400 ml) was added. Water (300 ml) was added and the organic layer was separated, dried (MgSO$_4$), filtered and the solvent was evaporated. The residue (28 g) was purified by column chromatography over silica gel (eluent: DCM/MeOH 95/5). The pure fractions were collected and the solvent was evaporated. The residue was crystallized from acetonitrile, filtered off and dried in vacuo, yielding 15.1 g of intermediate 1.

b) Preparation of intermediate 2

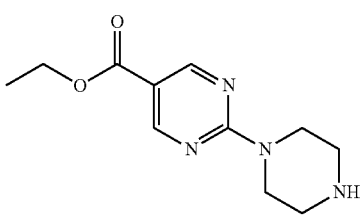

A mixture of intermediate 1 (0.03 mol) in EtOH (250 ml) was hydrogenated at 50° C. with Pd/C 10% (2 g) as a catalyst. After uptake of H$_2$ (1 equiv), the catalyst was filtered off and the filtrate was evaporated. The residue was purified by column chromatography over silica gel (eluent: DCM/(MeOH/NH$_3$) 90/10). The product fractions were collected and the solvent was evaporated, yielding 6.8 g (>96%) of intermediate 2.

c) Preparation of intermediate 3

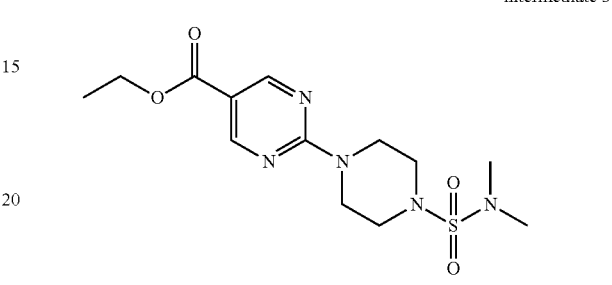

A solution of dimethyl-sulfamoyl chloride (0.0015 mol) in DCM (1 ml) was added at 5° C. to a mixture of intermediate 2 (0.0012 mol) and TEA (0.0017 mol) in DCM (1 ml) under N$_2$ flow. The mixture was stirred at room temperature for 18 hours. Potassium carbonate 10% was added. The mixture was extracted with DCM. The organic layer was separated, dried (MgSO$_4$), filtered, and the solvent was evaporated till dryness. The residue (0.69 g) was taken up in diethyl ether. The precipitate was filtered off and dried, yielding 0.64 g (73%) of intermediate 3, melting point 193° C.

Example A2

Preparation of intermediate 4

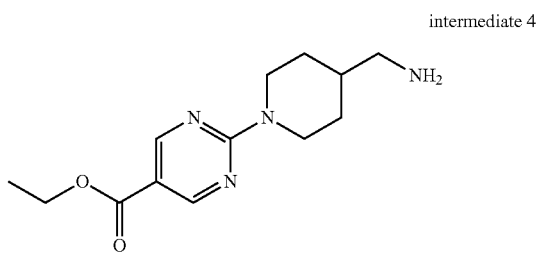 [SMILES: CCOC(=O)c1cnc(N2CCC(CN)CC2)nc1]

A solution of 2-(methylsulfonyl)-5-pyrimidinecarboxylic acid, ethyl ester (0.0434 mol) in acetonitrile (100 ml) was added dropwise at 10° C. to a solution of 4-piperidinemethanamine (0.0868 mol) and potassium carbonate (0.0434 mol) in acetonitrile (200 ml) under N$_2$ flow. The mixture was stirred at room temperature for 2 hours, poured out into ice water and extracted with DCM. The organic layer was separated, dried (MgSO$_4$), filtered, and the solvent was evaporated. The residue (14.18 g) was purified by column chromatography over silica gel (20-45 µm) (eluent: DCM/MeOH/NH$_4$OH 90/10/1 to 80/20/2). The pure fractions were collected and the solvent was evaporated, yielding 3.7 g (32%) of intermediate 4.

Example A3 a) Preparation of intermediate 5

A mixture of intermediate 2 (0.0002 mol), (-phenyl-benzeneacetyl chloride (0.0003 mol) and morpholinomethyl-PS-scavenger (Supplier Novabiochem cat No 01-64-0171: Morpholinomethyl polystyrene HL (200-400 mesh), 2% divinylbenzene) (0.150 g) in DCM (5 ml) was stirred at room temperature for 20 hours, then tris(2-aminoethyl)amine-PS-scavenger (Supplier Novabiochem cat No 01-64-0170: Tris-(2-aminomethyl)-amine polystyrene HL(200-400 mesh), 1% divinylbenzene) (0.150 g) was added and the reaction mixture was stirred for another 4 hours. The scavengers were filtered off, washed with DCM and the solvent was evaporated, yielding intermediate 5.

b) Preparation of intermediate 6

A mixture of intermediate 5 (0.0003 mol) in sodium hydroxide 1N (1.5 ml), THF (4 ml) and MeOH (1 ml) was stirred at room temperature for 3 days, then the reaction mixture was neutralised with HCl (1.5 ml, 1N). The mixture was filtered through Extrelut™ NT (supplier: Merck) and dried under N$_2$-flow, yielding intermediate 6.

c) Preparation of intermediate 7

A mixture of intermediate 6 (0.0003 mol), HOBT-6-carboxamidomethyl-PS-scavenger (0.200 g; Novabiochem Cat. No. 01-64-0425) and N,N-dimethyl-4-pyridinamine (0.00015 mol) in DCM/DMF (5 ml) was stirred at room temperature for 15 min., then N,N-methanetetraylbis-2-propanamine (0.070 ml) was added and the reaction mixture was shaken for 4 hours. The resin was washed 3 times with DCM, 3 times with DMF and again 3 times with DCM and 3 times with DMF, finally 6 times with DCM. A solution of O-(tetrahydro-2H-pyran-2-yl)-hydroxylamine (0.00026 mol) in DCM (5 ml) was added and the reaction mixture was shaken for 20 hours, then PS linked methylisocyanate (Supplier Novabiochem cat No 01-64-0289: Methylisothiocyanate polystyrene HL(200-400 mesh), 2% divinylbenzene) (0.150 g) was added and the mixture was shaken for 4 hours. The scavengers were filtered off, washed 2 times with DCM and the filtrate was used, yielding intermediate 7.

B. PREPARATION OF THE FINAL COMPOUNDS

Example B1

N-Fmoc-hydroxylamine 2-chlorotrityl resin (Novabiochem, 01-64-0165) was deprotected by 50% piperidine in DMF (RT, 24 hr). The resin was washed several times with DCM and DMF and swelled in DMF. Two equivalents of acid[1], PyBrOP and 4 equivalents of DIEA were added as one portion. The mixture was shaken for 24 hr, liquid was drained and the resin was washed several times by DCM and DMF. The resin was swelled in DMF containing 2 equivalents of amine, was shaken 24 hr at RT, the liquid was drained and the resin was washed by DCM and DMF. An arylsulfonyl chloride (2 eq.) was added as one portion to the resin swelled in DMF with 4 equivalents of TEA. Reaction was stirred overnight, drained and the resin was washed by DCM and DMF. The final product was cleaved by 5% TFA in DCM, analyzed by HPLC and MS and evaporated in the pre-weighted test-tubes.

[1]. Based on the loading of the resin.

For illustrative purposes the scheme hereunder is included.

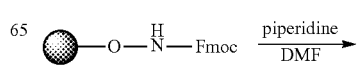

-continued

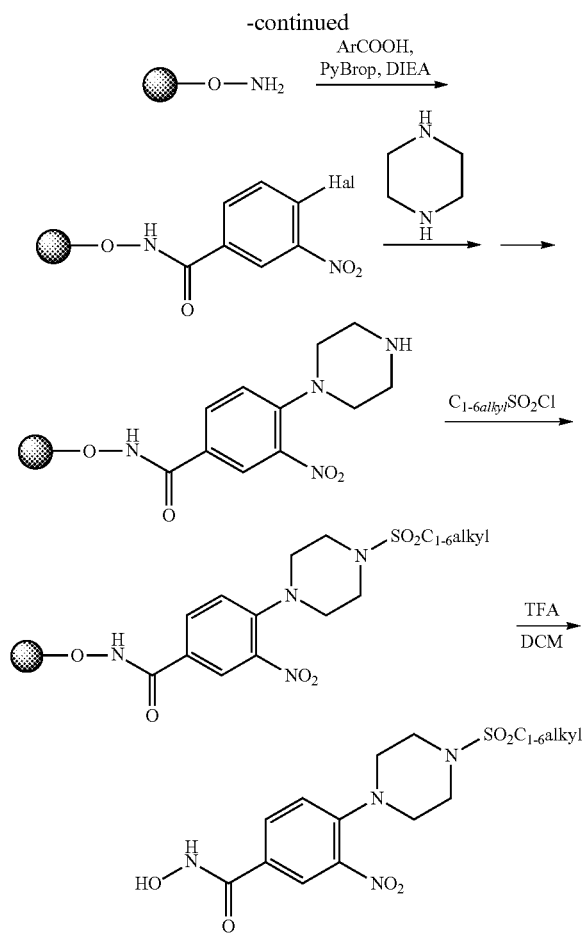

Example B2

N-Fmoc-hydroxylamine 2-chlorotrityl resin (Novabiochem, 01-64-0165) was deprotected by 50% piperidine in DMF (RT, 24 hr)[1]. The resin was washed[2] several times with DCM and DMF and swelled in DMF. Two equivalents of acid[3], PyBrOP[4] and 4 equivalents of DIEA were added as one portion. The mixture was shaken for 24 hr, liquid was drained and the resin was washed several times by DCM and DMF. The resin was swelled in DMF containing 2 equivalents of amine, was shaken 24 hr at RT, the liquid was drained and the resin was washed by DCM and DMF. The final product was cleaved by 5% TFA in DCM, analyzed by HPLC and MS and evaporated in the pre-weighted test-tubes.

[1]. In one example compound 1 carboxymethanethiol 4-methoxytrityl resin (Novabiochem, 01-64-0238) was used.
[2]. In one case also MeOH was used in the different washing procedures compound 1.
[3]. Based on the loading of the resin.
[4]. In one case PyBrOP was replaced by PyBOP compound 1.

Example B3

N-Fmoc-hydroxylamine 2-chlorotrityl resin (Novabiochem, 01-64-0165) was deprotected by 50% piperidine in DMF (RT, 24 hr)[1]. The resin was washed[2] several times with DCM and DMF and swelled in DMF. Two equivalents of acid[3], PyBrOP[4] and 4 equivalents of DIEA were added as one portion. The mixture was shaken for 24 hr, liquid was drained and the resin was washed several times by DCM and DMF. The resin was swelled in DMF containing 2 equivalents of amine, was shaken 24 hr at RT, the liquid was drained and the resin was washed by DCM and DMF. Three equivalents of acid, DIC and DIEA were shaken with resin overnight at RT. The resin was drained and washed by DCM and DMF. The final product was cleaved by 5% TFA in DCM, analyzed by HPLC and MS and evaporated in the pre-weighted test-tubes.

Example B4 a) Preparation of

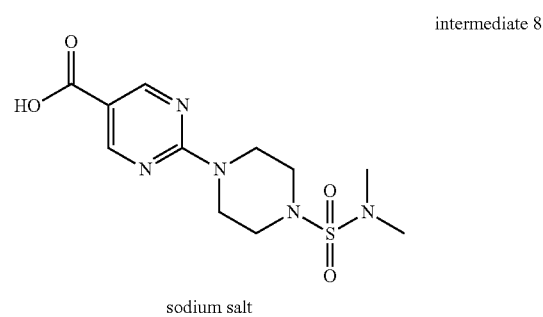 [SMILES: CN(C)S(=O)(=O)N1CCN(c2ncc(C(=O)O)cn2)CC1]

intermediate 8 sodium salt

A mixture of intermediate 3 (0.0016 mol) and sodium Hydroxide (0.0033 mol) in EtOH (6 ml) was stirred and refluxed for 2 hours, then cooled to room temperature. The precipitate was filtered, washed with EtOH and dried, yielding 0.59 g (>100%) of intermediate 8.Na.

b) Preparation of

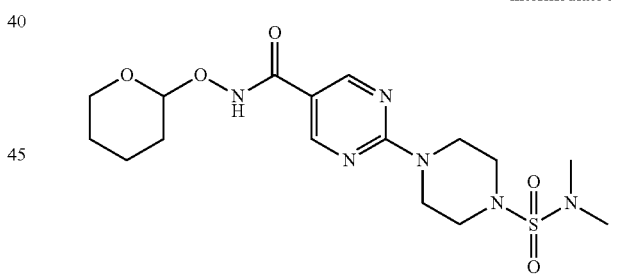

intermediate 9

N'-(ethylcarbonimidoyl)-N,N-dimethyl-1,3-propanediamine, monohydrochloride (0.0021 mol) was added portionwise to a mixture of intermediate 8.Na (0.0016 mol), O-(tetrahydro-2H-pyran-2-yl)-hydroxylamine (0.0021 mol) and 1-hydroxy-1H-benzotriazole (0.0021 mol) in DCM/THF (10 ml) under $N_2$ flow. The mixture was stirred at room temperature for a week end. Potassium carbonate 10% was added. The mixture was extracted with DCM. The organic layer was separated, dried (MgSO$_4$), filtered, and the solvent was evaporated till dryness. The residue (0.94 g) was purified by column chromatography over kromasil (eluent: DCM/MeOH/NH$_4$OH 97/3/0.1; 15-40 µm). The pure fractions were collected and the solvent was evaporated. The residue (0.45 g, 65%) was taken up in diethyl ether. The precipitate was filtered off and dried, yielding 0.422 g (61%) of intermediate 9, melting point 183° C.

c) Preparation of compound 2

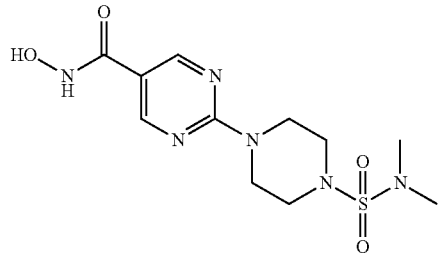

Trifluoroacetic acid (0.5 ml) was added to a mixture of intermediate 9 (0.0009 mol) in MeOH (10 ml). The mixture was stirred at room temperature for 18 hours. The precipitate was filtered, washed with DCM and dried, yielding 0.176 g (59%) of compound 2, melting point>260° C.

Example B5

Preparation of intermediate 10

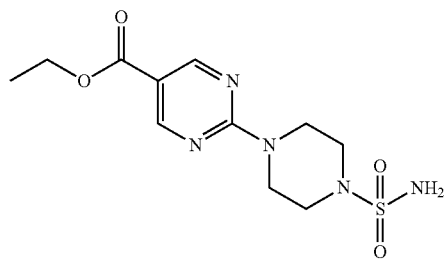

A mixture of intermediate 2 (0.0019 mol) and sulfamide (0.0021 mol) in 1,2-dimethoxy-ethane (5 ml) was stirred and refluxed for 4 days. Water was added. The mixture was filtered off and dried, yielding 0.51 g (83%) of intermediate 10, melting point 192° C.

Intermediate 10 was handled analogously as described in example [B4] to give 0.034 g (13%) of compound 3, melting point 212° C.

compound 3

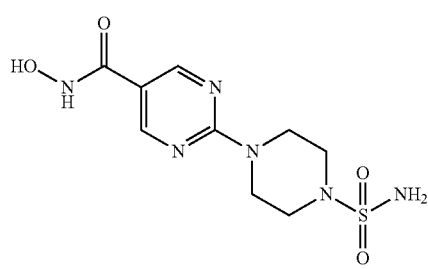

Example B6

Preparation of intermediate 11

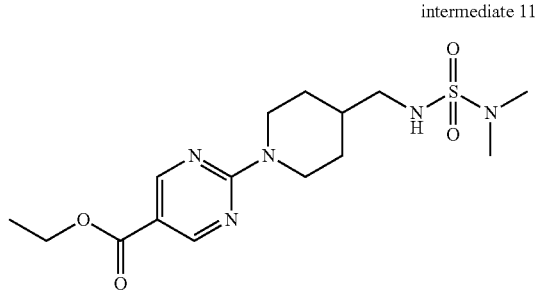 [SMILES: CCOC(=O)c1cnc(N2CCC(CNS(=O)(=O)N(C)C)CC2)nc1]

A solution of dimethyl-sulfamoyl chloride (0.007 mol) in DCM (5 ml) was added at 10° C. to a solution of intermediate 4 (0.0057 mol) and TEA (0.0085 mol) in DCM (5 ml) under $N_2$ flow. The mixture was stirred overnight, poured out into ice water and extracted with DCM. The organic layer was separated, dried ($MgSO_4$), filtered, and the solvent was evaporated. The residue was crystallized from $CH_3CN$/diethyl ether. The precipitate was filtered off and dried, yielding 0.492 g (24%) of intermediate 11, melting point 142° C.

Intermediate 11 was handled analogously as described in example [B4] to give 0.7 g (85%) of compound 4, melting point 182° C.

compound 4

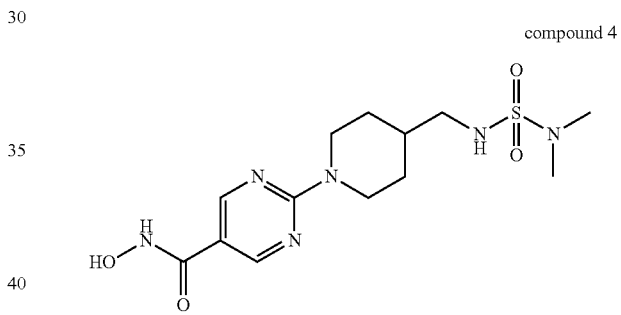

Example B7

Preparation of compound 5

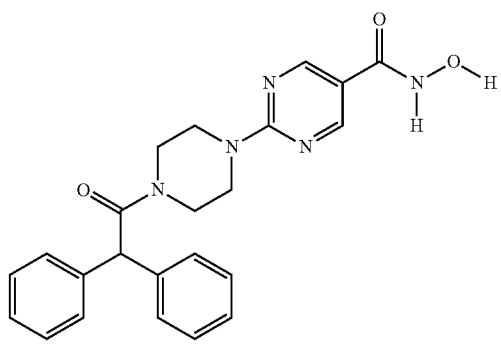

A mixture of intermediate 7 (0.0003 mol) in acetic acid, trifluoro-acetic acid (5 ml, 5% in MeOH) was stirred at room temperature for 20 hours, then the reaction mixture was blown dry, yielding compound 5.

Example B8

Preparation of

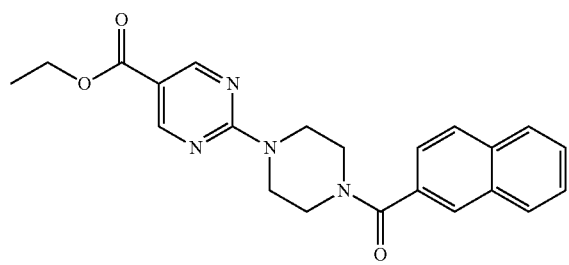

intermediate 12

A mixture of intermediate 2 (0.0025 mol), 2-naphthalenecarbonyl chloride (0.003 mol) and potassium carbonate (0.005 mol) in acetonitrile (20 ml) was stirred and refluxed overnight, then cooled to room temperature, poured out into ice water and extracted with DCM. The organic layer was separated, dried (MgSO$_4$), filtered, and the solvent was evaporated. The residue was crystallized from diethyl ether. The precipitate was filtered off and dried, yielding 0.97 g (100%) of intermediate 12, melting point 140° C. Intermediate 12 was handled analogously as described in example [B4] to give 0.338 g (86%) of compound 6, melting point 130° C.

compound 6

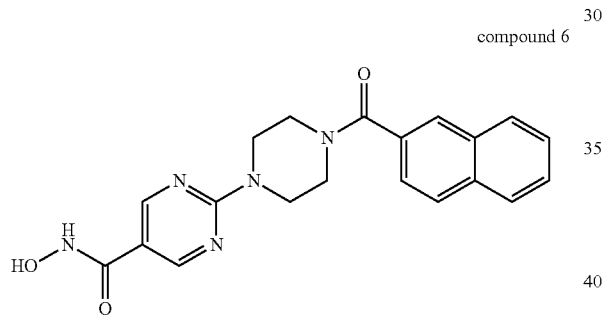

Table F-1 lists the compounds that were prepared according to one of the above Examples. The following abbreviations were used in the tables. Co.No. stands for Compound Number, Ex. [Bn°] referred to the same method as described in the Bn° examples, C$_2$HF$_3$O$_2$ stands for the trifluoroacetate salt. Some compounds have been characterized via melting point (mp.), other compounds were characterized via Mass Spectral data [MH$^+$] (ms.).

TABLE F-1

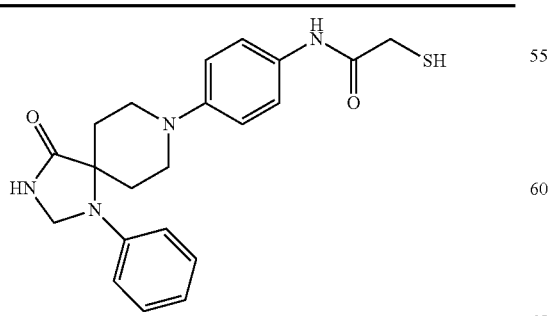

C$_2$HF$_3$O$_2$ (1:1), Co. No. 1; Ex. [B2]

TABLE F-1-continued

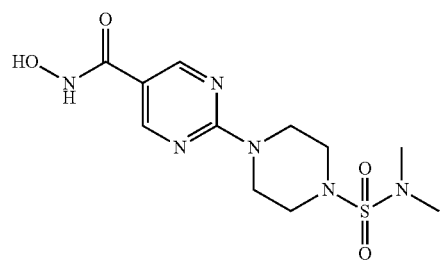

Co. No. 2; Ex. [B4]; mp >260° C.

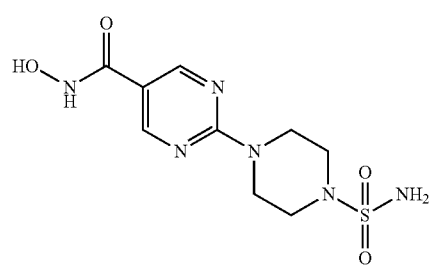

Co. No. 3; Ex. [B5]; mp 212° C.

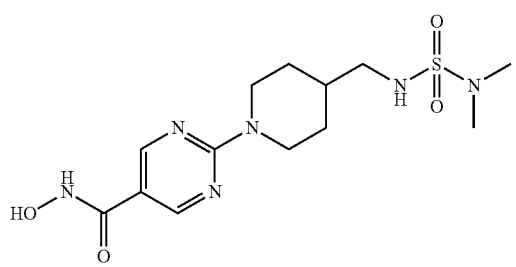

Co. No. 4; Ex. [B6]; mp 182° C.

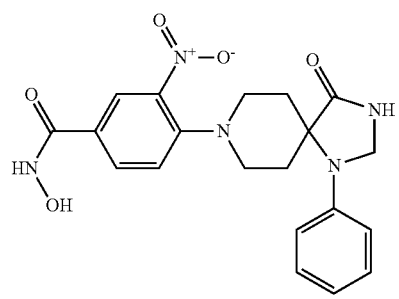

•C$_2$HF$_3$O$_2$ (1:2), Co. No. 7; Ex. [B2]; ms. 412

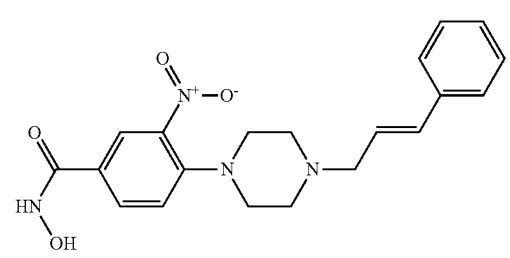

•C$_2$HF$_3$O$_2$ (1:2), Co. No. 8; Ex. [B2] ms. 383

TABLE F-1-continued
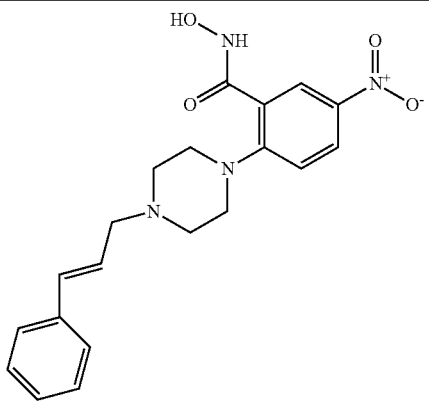
•C₂HF₃O₂ (1:2), Co. No. 9; Ex. [B2]; ms. 383
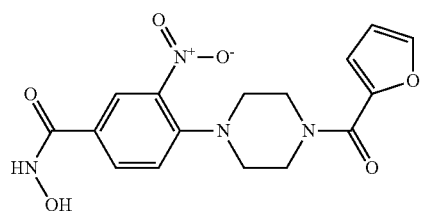
•C₂HF₃O₂ (1:1), Co. No. 10; Ex. [B2]; ms. 361
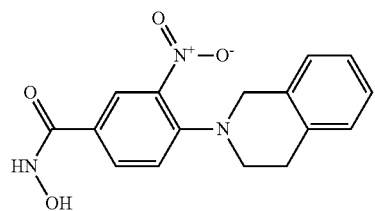
•C₂HF₃O₂ (1:1), Co. No. 11; Ex. [B2]; ms. 314
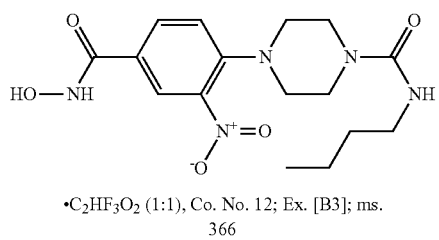
•C₂HF₃O₂ (1:1), Co. No. 12; Ex. [B3]; ms. 366
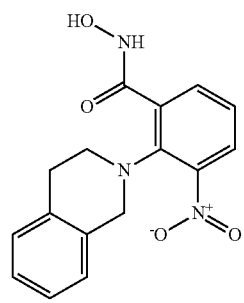
•C₂HF₃O₂ (1:1), Co. No. 13; Ex. [B2]; ms. 314
TABLE F-1-continued
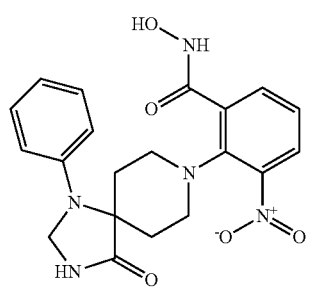
•C₂HF₃O₂ (1:1), Co. No. 14; Ex. [B2]; ms. 412
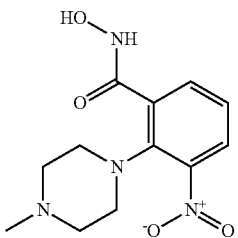
C₂HF₃O₂ (1:2), Co. No. 15; Ex. [B2]; ms. 281
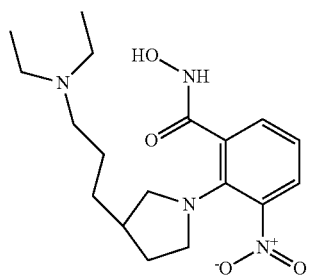
C₂HF₃O₂ (1:2), Co. No. 16; Ex. [B2]; ms. 365
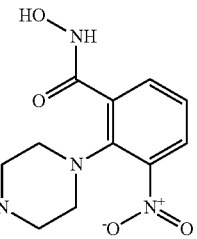
C₂HF₃O₂ (1:2), Co. No. 17; Ex. [B2]; ms. 295
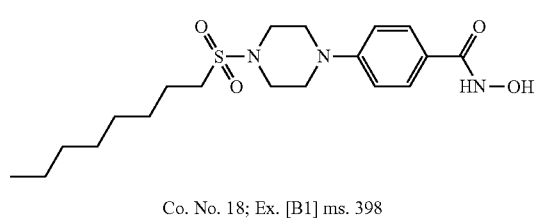 [SMILES: CCCCCCCCS(=O)(=O)N1CCN(c2ccc(C(=O)NO)cc2)CC1]
Co. No. 18; Ex. [B1] ms. 398

TABLE F-1-continued
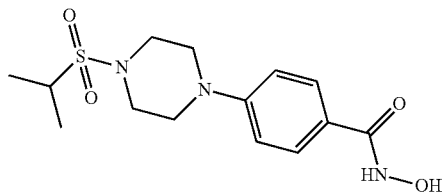
Co. No. 19; Ex. [B1]; ms. 328
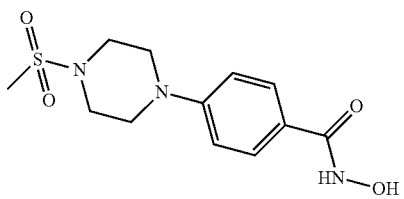
Co. No. 20; Ex. [B1]; ms. 300
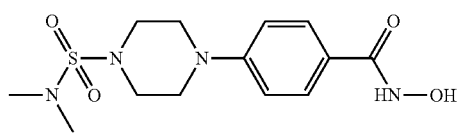
Co. No. 21; Ex. [B1]; ms. 329
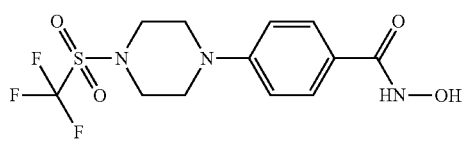
Co. No. 22; Ex. [B1]; ms. 354
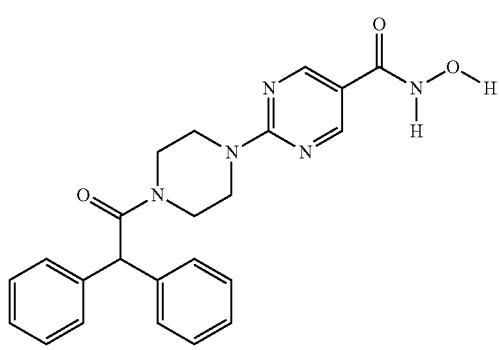
Co. No. 5; Ex. [B7]; ms. 418
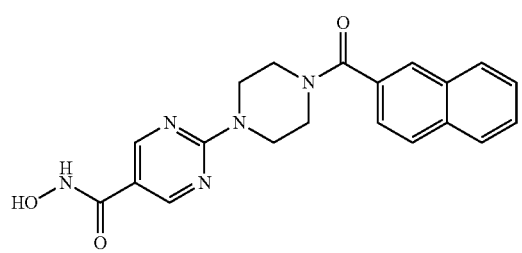
Co. No. 6; Ex. [B8]; mp. 130° C.
TABLE F-1-continued
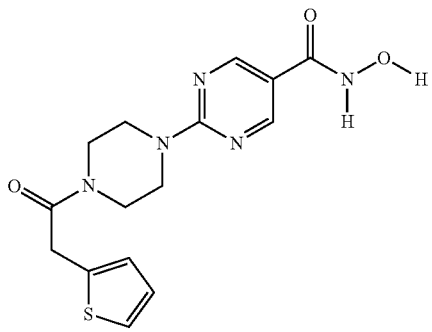
Co. No. 23; Ex. [B7]; ms. 348
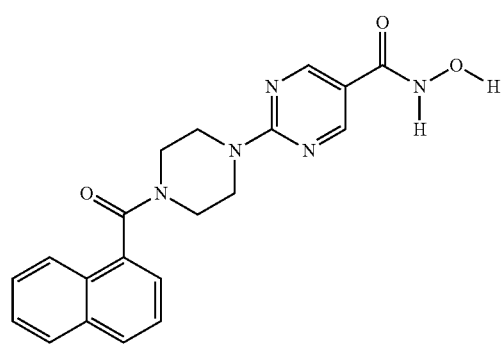
Co. No. 24; Ex. [B7]; ms. 378
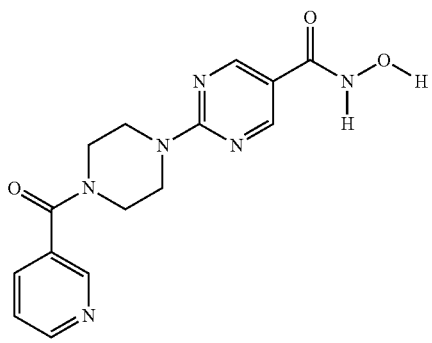
Co. No. 25; Ex. [B7]; ms. 329
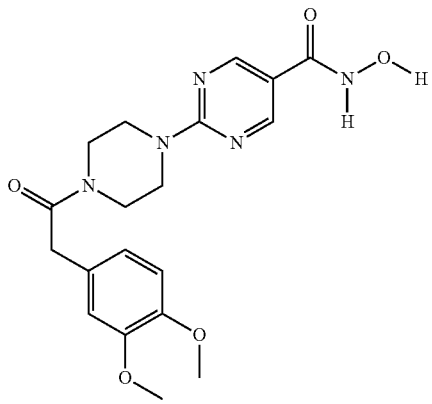
Co. No. 26; Ex. [B7]; ms. 402

TABLE F-1-continued

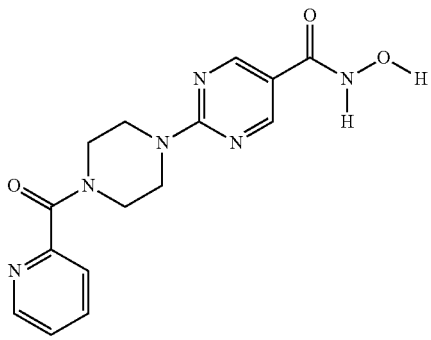

Co. No. 27; Ex. [B7]; ms. 329

C. PHARMACOLOGICAL EXAMPLE

The in vitro assay for inhibition of histone deacetylase (see example C.1) measures the inhibition of HDAC enzymatic activity obtained with the compounds of formula (I).

Cellular activity of the compounds of formula (I) was determined on A2780 tumour cells using a colorimetric assay for cell toxicity or survival (Mosmann Tim, Journal of Immunological Methods 65: 55-63, 1983)(see example C.2).

Kinetic solubility in aqueous media measures the ability of a compound to stay in aqueous solution upon dilution (see example C.3).

DMSO-stock solutions are diluted with a single aqueous buffer solvent in 3 consecutive steps. For every dilution turbidity is measured with a nephelometer.

A drug's permeability expresses its ability to move from one medium into or through another. Specifically its ability to move through the intestinal membrane into the blood stream and/or from the blood stream into the target. Permeability (see example C.4) can be measured through the formation of a filter-immobilized artificial membrane phospholipid bilayer. In the filter-immobilized artificial membrane assay, a "sandwich" is formed with a 96-well microtitre plate and a 96-well filter plate, such that each composite well is divided into two chambers with a donor solution at the bottom and an acceptor solution at the top, separated by a 125 µm microfilter disc (0.45 µm pores), coated with 2% (wt/v) dodecane solution of dioleoylphosphatidyl-choline, under conditions that multi-lamellar bilayers form inside the filter channels when the system contacts an aqueous buffer solution. The permeability of compounds through this artificial membrane is measured in cm/s. The purpose is to look for the permeation of the drugs through a parallel artificial membrane at 2 different pH's: 4.0 and 7.4. Compound detection is done with UV-spectrometry at optimal wavelength between 250 and 500 nm.

Metabolism of drugs means that a lipid-soluble xenobiotic or endobiotic compound is enzymatically transformed into (a) polar, water-soluble, and excretable metabolite(s). The major organ for drug metabolism is the liver. The metabolic products are often less active than the parent drug or inactive. However, some metabolites may have enhanced activity or toxic effects. Thus drug metabolism may include both "detoxication" and "toxication" processes. One of the major enzyme systems that determine the organism's capability of dealing with drugs and chemicals is represented by the cytochrome P450 monooxygenases, which are NADPH dependent enzymes. Metabolic stability of compounds can be determined in vitro with the use of subcellular human tissue (see example C.5). Here metabolic stability of the compounds is expressed as % of drug metabolised after 15 minutes incubation of these compounds with microsomes. Quantitation of the compounds was determined by LC-MS analysis.

The tumour suppressor p53 transcriptionally activates a number of genes including the WAF1/CIP1 gene in response to DNA damage. The 21 kDa product of the WAF1 gene is found in a complex involving cyclins, cyclin dependent kinases (CDKs), and proliferating cell nuclear antigen (PCNA) in normal cells but not transformed cells and appears to be a universal inhibitor of CDK activity. One consequence of p21WAF1 binding to and inhibiting CDKs is to prevent CDK-dependent phosphorylation and subsequent inactivation of the Rb protein, which is essential for cell cycle progression. Induction of p21WAF1 in response to cellular contact with a HDAC inhibitor is therefore a potent and specific indicator of inhibition of cell cycle progression at both the G1 and G2 checkpoints.

The capacity of the compounds to induce p21WAF1 was measured with the p21WAF1 enzyme linked immunosorbent assay (WAF1 ELISA of Oncogene). The p21 WAF1 assay is a "sandwich" enzyme immunoassay employing both mouse monoclonal and rabbit polyclonal antibodies. A rabbit polyclonal antibody, specific for the human WAF1 protein, has been immobilized onto the surface of the plastic wells provided in the kit. Any p21WAF present in the sample to be assayed will bind to the capture antibody. The biotinylated detector monoclonal antibody also recognizes human p21WAF1 protein, and will bind to any p21WAF1, which has been retained by the capture antibody. The detector antibody, in turn, is bond by horseradish peroxidas-conjugated streptavidin. The horseradish peroxidase catalyses the conversion of the chromogenic substrate tetra-methylbenzidine from a colorless solution to a blue solution (or yellow after the addition of stopping reagent), the intensity of which is proportional to the amount of p21WAF1 protein bond to the plate. The colored reaction product is quantified using a spectrophotometer. Quantitation is achieved by the construction of a standard curve using known concentrations of p21WAF1 (provided lyophilised)(see example C.6).

Example C.1

In Vitro Assay for Inhibition of Histone Deacetylase

HeLa nuclear extracts (supplier: Biomol) were incubated at 60 µg/ml with $2\times10^{-8}$ M of radiolabeled peptide substrate. As a substrate for measuring HDAC activity a synthetic peptide, i.e. the amino acids 14-21 of histone H4, was used. The substrate is biotinylated at the $NH_2$-terminal part with a 6-aminohexanoic acid spacer, and is protected at the COOH-terminal part by an amide group and specifically [$^3$H]acetylated at lysine 16. The substrate, biotin-(6-aminohexanoic) Gly-Ala-([$^3$H]-acetyl-Lys-Arg-His-Arg-Lys-Val-$NH_2$), was added in a buffer containing 25 mM Hepes, 1M sucrose, 0.1 mg/ml BSA and 0.01% Triton X-100 at pH 7.4. After 30 min the deacetylation reaction was terminated by the addition of HCl and acetic acid. (final concentration 0.035 mM and 3.8 mM respectively). After stopping the reaction, the free $^3$H-acetate was extracted with ethylacetate. After mixing and centrifugation, the radioactivity in an aliquot of the upper (organic) phase was counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-12}$M. In each test the blank value was subtracted from both the control and the sample values. The control sample represented 100% of substrate deactylation. For each sample the radioactivity was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value). All tested compounds showed enzymatic activity at a test concentration of $10^{-5}$M and 21 compounds had a $pIC_{50} \geq 5$ (see table F-2).

Example C.2

Determination of Antiproliferative Activity on A2780 Cells

All compounds tested were dissolved in DMSO and further dilutions were made in culture medium. Final DMSO concentrations never exceeded 0.1% (v/v) in cell proliferation assays. Controls contained A2780 cells and DMSO without compound and blanks contained DMSO but no cells. MTT was dissolved at 5 mg/ml in PBS. A glycine buffer comprised of 0.1M glycine and 0.1M NaCl buffered to pH 10.5 with NaOH (1N) was prepared (all reagents were from Merck).

The human A2780 ovarian carcinoma cells (a kind gift from Dr. T. C. Hamilton [Fox Chase Cancer Centre, Pennsylvania, USA]) were cultured in RPMI 1640 medium supplemented with 2 mM L-glutamine, 50 µg/ml gentamicin and 10% fetal calf serum. Cells were routinely kept as monolayer cultures at 37° C. in a humidified 5% $CO_2$ atmosphere. Cells were passaged once a week using a trypsin/EDTA solution at a split ratio of 1:40. All media and supplements were obtained from Life Technologies. Cells were free of mycoplasma contamination as determined using the Gen-Probe *Mycoplasma* Tissue Culture kit (supplier: BioMérieux).

Cells were seeded in NUNC™ 96-well culture plates (Supplier: Life Technologies) and allowed to adhere to the plastic overnight. Densities used for plating were 1500 cells per well in a total volume of 200 µl medium. After cell adhesion to the plates, medium was changed and drugs and/or solvents were added to a final volume of 200 µl. Following four days of incubation, medium was replaced by 200 µl fresh medium and cell density and viability was assessed using an MTT-based assay. To each well, 25 µl MTT solution was added and the cells were further incubated for 2 hours at 37° C. The medium was then carefully aspirated and the blue MTT-formazan product was solubilized by addition of 25 µl glycine buffer followed by 100 µl of DMSO. The microtest plates were shaken for 10 min on a microplate shaker and the absorbance at 540 nm was measured using an Emax 96-well spectrophotometer (Supplier: Sopachem).

Within an experiment, the results for each experimental condition are the mean of 3 replicate wells. For initial screening purposes, compounds were tested at a single fixed concentration of $10^{-6}$M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value). Most of the tested compounds showed cellular activity at a test concentration of $10^{-6}$ M and 9 compounds had a $pIC_{50} \geq 5$ (see table F-2)

Example C.3

Kinetic Solubility in Aqueous Media

In the first dilution step, 10 µl of a concentrated stock-solution of the active compound, solubilized in DMSO (5 mM), was added to 100 µl phosphate citrate buffer pH 7.4 and mixed. In the second dilution step, an aliquot (20 µl) of the first dilution step was further dispensed in 100 µl phosphate citrate buffer pH 7.4 and mixed. Finally, in the third dilution step, a sample (20 µl) of the second dilution step was further diluted in 100 µl phosphate citrate buffer pH 7.4 and mixed. All dilutions were performed in 96-well plates. Immediately after the last dilution step the turbidity of the three consecutive dilution steps were measured with a nephelometer. Dilution was done in triplicate for each compound to exclude occasional errors. Based on the turbidity measurements a ranking is performed into 3 classes. Compounds with high solubility obtained a score of 3 and for this compounds the first dilution is clear. Compounds with medium solubility obtained a score of 2. For these compounds the first dilution is unclear and the second dilution is clear. Compounds with low solubility obtained a score of 1 and for these compounds both the first and the second dilution are unclear. The solubility of 9 compounds was measured. From these compounds 7 showed a score of 3, and 2 demonstrated a score of 1 (see table F-2).

Example C.4

Parallel Artificial Membrane Permeability Analysis

The stock samples (aliquots of 10 µl of a stock solution of 5 mM in 100% DMSO) were diluted in a deep-well or Premix plate containing 2 ml of an aqueous buffer system pH 4 or pH 7.4 (PSR4 System Solution Concentrate (pION)).

Before samples were added to the reference plate, 150 µl of buffer was added to wells and a blank UV-measurement was performed. Thereafter the buffer was discarded and the plate was used as reference plate. All measurements were done in UV-resistant plates (supplier: Costar or Greiner).

After the blank measurement of the reference plate, 150 µl of the diluted samples was added to the reference plate and 200 µl of the diluted samples was added to donor plate 1. An acceptor filter plate 1 (supplier: Millipore, type:MAIP N45) was coated with 4 µl of the artificial membrane-forming solution (1,2-Dioleoyl-sn-Glycer-3-Phosphocholine in Dodecane containing 0.1% 2,6-Di-tert-butyl-4-methylphenol and placed on top of donor plate 1 to form a "sandwich". Buffer (200 µl) was dispensed into the acceptor wells on the top. The sandwich was covered with a lid and stored for 18 h at room temperature in the dark.

A blank measurement of acceptor plate 2 was performed through the addition of 150 µl of buffer to the wells, followed by an UV-measurement. After the blank measurement of acceptor plate 2 the buffer was discarded and 150 μl of acceptor solution was transferred from the acceptor filter plate 1 to the acceptor plate 2. Then the acceptor filter plate 1 was removed form the sandwich. After the blank measurement of donor plate 2 (see above), 150 μl of the donor solution was transferred from donor plate 1 to donor plate 2. The UV spectra of the donor plate 2, acceptor plate 2 and reference plate wells were scanned (with a SpectraMAX 190). All the spectra were processed to calculate permeability with the PSR4p Command Software. All compounds were measured in triplo. Carbamazepine, griseofulvin, acycloguanisine, atenolol, furosemide, and chlorothiazide were used as standards in each experiment. Compounds were ranked in 3 categories as having a low permeability (mean effect<$0.5×10^{-6}$ cm/s; score 1), a medium permeability ($1×10^{-6}$ cm/s>mean effect≥$0.5×10^{-6}$ cm/s; score 2) or a high permeability (≥$0.5×10^{-6}$ cm/s; score 3). Two compounds showed a score of 1 at one of the pH's measured.

Example C.5

Metabolic Stability

Sub-cellular tissue preparations were made according to Gorrod et al. (Xenobiotica 5: 453-462, 1975) by centrifugal separation after mechanical homogenization of tissue.

Liver tissue was rinsed in ice-cold 0.1M Tris-HCl (pH 7.4) buffer to wash excess blood. Tissue was then blotted dry, weighed and chopped coarsely using surgical scissors. The tissue pieces were homogenized in 3 volumes of ice-cold 0.1M phosphate buffer (pH 7.4) using either a Potter-S (Braun, Italy) equipped with a Teflon pestle or a Sorvall Omni-Mix homogeniser, for 7×10 sec. In both cases, the vessel was kept in/on ice during the homogenization process.

Tissue homogenates were centrifuged at 9000×g for 20 minutes at 4° C. using a Sorvall centrifuge or Beckman Ultracentrifuge. The resulting supernatant was stored at −80° C. and is designated 'S9'.

The S9 fraction can be further centrifuged at 100.000×g for 60 minutes (4° C.) using a Beckman ultracentrifuge. The resulting supernatant was carefully aspirated, aliquoted and designated 'cytosol'. The pellet was re-suspended in 0.1M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 min at 95 degrees Celsius) microsomes. Recovery of the compounds in the control samples was always 100%.

The mixtures were preincubated for 5 min at 37 degrees Celsius. The reaction was started at timepoint zero (t=0) by addition of 0.8 mM NADP and the samples were incubated for 15 min (t=15). The reaction was terminated by the addition of 2 volumes of DMSO. Then the samples were centrifuged for 10 min at 900×g and the supernatants were stored at room temperature for no longer as 24 h before analysis. All incubations were performed in duplo. Analysis of the supernatants was performed with LC-MS analysis. Elution of the samples was performed on a Xterra MS C 18 (50×4.6 mm, 5 μm, Waters, US). An Alliance 2790 (Supplier: Waters, US) HPLC system was used. Elution was with buffer A (25 mM ammoniumacetate (pH 5.2) in H$_2$O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 min in a linear fashion and organic phase concentration was kept stationary for an additional 1.5 min. Total injection volume of the samples was 25 μl.

A Quattro (supplier: Micromass, Manchester, UK) triple quadrupole mass spectrometer fitted with and ESI source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 sec.

Metabolic stability was expressed as % metabolism of the compound after 15 min of incubation in the presence of active microsomes $$(E(\text{act}))(\% \text{ metabolism} = 100\% - \left(\left(\frac{\text{Total Ion Current } (TIC) \text{ of } E(\text{act}) \text{ at } t = 15}{TIC \text{ of } E(\text{act}) \text{ at } t = 0}\right) \times 100\right).$$

Compounds that had a percentage metabolism less than 20% were defined as highly metabolic stable. Compound that had a metabolism between 20 and 70% were defined as intermediately stable and compounds that showed a percentage metabolism higher than 70 were defined as low metabolic stable. Three reference compounds were always included whenever a metabolic stability screening was performed. Verapamil was included as a compound with low metabolic stability (% metabolism=73%). Cisapride was included as a compound with medium metabolic stability (% metabolism 45%) and propanol was included as a compound with intermediate to high metabolic stability (25% metabolism). These reference compounds were used to validate the metabolic stability assay.

One compound was tested and showed a percentage metabolism less than 20%.

Example C.6 p21 Induction Capacity

The following protocol has been applied to determine the p21 protein expression level in human A2780 ovarian carcinoma cells. The A2780 cells (20000 cells/180 μl) were seeded in 96 microwell plates in RPMI 1640 medium supplemented with 2 mM L-glutamine, 50 μg/ml gentamicin and 10% fetal calf serum. 24 hours before the lysis of the cells, compounds were added at final concentrations of $10^{-5}$, $10^{-6}$, $10^{-7}$ and $10^{-8}$ M. All compounds tested were dissolved in DMSO and further dilutions were made in culture medium. 24 hours after the addition of the compound, the supernatants were removed from the cells. Cells were washed with 200 μl ice-cold PBS. The wells were aspirated and 30 μl of lysis buffer (50 mM Tris.HCl (pH 7.6), 150 mM NaCl, 1% Nonidet p40 and 10% glycerol) was added. The plates were incubated overnight at −70° C.

The appropriate number of microtiter wells were removed from the foil pouch and placed into an empty well holder. A working solution (1×) of the Wash Buffer (20× plate wash concentrate: 100 ml 20-fold concentrated solution of PBS and surfactant. Contains 2% chloroacetamide) was prepared. The lyophilised p21 WAF standard was reconstituted with distilled H$_2$O and further diluted with sample diluent (provided in the kit)

The samples were prepared by diluting them 1:4 in sample diluent. The samples (100 μl) and the p21WAF1 standards (100 μl) were pipetted into the appropriate wells and incubated at room temperature for 2 hours. The wells were washed 3 times with 1× wash buffer and then 100 μl of detector antibody reagent (a solution of biotinylated monoclonal p21WAF1 antibody) was pipetted into each well. The wells were incubated at room temperature for 1 hour and then washed three times with 1× wash buffer. The 400× conjugate (peroxidase streptavidine conjugate: 400-fold concentrated solution) was diluted and 100 μl of the 1× solution was added to the wells. The wells were incubated at room temperature for 30 min and then washed 3 times with 1× wash buffer and 1 time with distilled H₂O, Substrate solution (chromogenic substrate)(100 μl) was added to the wells and the wells were incubated for 30 minutes in the dark at room temperature. Stop solution was added to each well in the same order as the previously added substrate solution. The absorbance in each well was measured using a spectrophotometric plate reader at dual wavelengths of 450/595 nm. For each experiment, controls (containing no drug) and a blank incubation (containing no cells or drugs) were run in parallel. The blank value was subtracted from all control and sample values. For each sample, the value for p21WAF1 induction (in absorbance units) was expressed as the percentage of the value for p21WAF1 present in the control. Percentage induction higher than 130% was defined as significant induction. Three compounds were tested in this assay. Two showed significant induction.

TABLE F-2

Table F-2 lists the results of the compounds that were tested according to example C.1, C.2, and C.3.

| Co. No. | Enzyme activity pIC50 | Cellular activity pIC50 | Solubility Score |
|---|---|---|---|
| 8 | >5 | | |
| 7 | >5 | | |
| 9 | >5 | | |
| 10 | >5 | | |
| 11 | >5 | | |
| 12 | >5 | | |
| 1 | <5 | <5 | 1 |
| 18 | 6.173 | 6.166 | 1 |
| 5 | 7.096 | 6.181 | |
| 23 | 6.932 | 5.796 | |
| 24 | 7.073 | 6.084 | |
| 25 | 6.29 | <5 | |
| 26 | 6.984 | 5.378 | |
| 27 | 6.433 | <5 | |
| 6 | 7.104 | 5.828 | 3 |
| 19 | 5.536 | <5 | 3 |
| 20 | 5.451 | <5 | |
| 21 | 5.679 | <5 | 3 |
| 22 | 5.599 | 5.297 | 3 |
| 2 | 6.615 | 5.534 | 3 |
| 3 | 6.881 | <5 | 3 |
| 4 | 7.27 | 5.528 | 3 |

D. COMPOSITION EXAMPLE

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I),

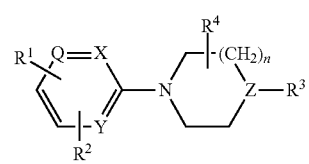

the N-oxide forms, the pharmaceutically acceptable addition salts and the stereo-chemically isomeric forms thereof, wherein n is 0, 1, 2 or 3 and when n is 0 then a direct bond is intended;

Q is

X is

Y is

Z is

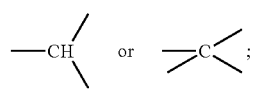

$R^1$ is —C(O)NR$^5$R$^6$, —N(H)C(O)R$^7$, —C(O)—C$_{1-6}$alkanediylSR$^7$, —NR$^8$C(O)N(OH)R$^7$, —NR$^8$C(O)C$_{1-6}$alkanediylSR$^7$, or —NR$^8$C(O)C=N(OH)R$^7$ wherein $R^5$ and $R^6$ are each independently hydrogen, hydroxy, C$_{1-6}$alkyl, hydroxyC$_{1-6}$alkyl, aminoC$_{1-6}$alkyl or aminoaryl;

$R^7$ is hydrogen, C$_{1-6}$alkyl, C$_{1-6}$alkylcarbonyl, arylC$_{1-6}$alkyl, C$_{1-6}$alkylpyrazinyl, pyridinone, pyrrolidinone or methylimidazolyl;

$R^8$ is hydrogen or $C_{1-6}$alkyl;
$R^2$ is hydrogen, halo, hydroxy, amino, nitro, $C_{1-6}$alkyl, $C_{1-6}$alkyloxy, trifluoromethyl, di($C_{1-6}$alkyl)amino, hydroxyamino or naphtalenylsulfonylpyrazinyl;
$R^3$ and $R^4$ are present on the same carbon atom, and $R^3$ and $R^4$ together form a bivalent radical of formula —C(O)—NH—CH$_2$—NR$^{10}$ (a-1)

wherein $R^{10}$ is hydrogen or aryl;
aryl in the above is phenyl, or phenyl substituted with one or more substituents that are each independently halo, $C_{1-6}$alkyl, $C_{1-6}$alkyloxy, trifluoromethyl, cyano or hydroxycarbonyl.

2. The compound as claimed in claim 1 wherein
n is 0 or 1;
$R^1$ is —C(O)NH(OH) or —NHC(O)$C_{1-6}$alkanediylSH;
$R^2$ is hydrogen or nitro;
and
$R^3$ and $R^4$ are present on the same carbon atom, and $R^3$ and $R^4$ together form a bivalent radical of formula (a-1) wherein $R^{10}$ is aryl.

3. The compound according to claim 1 that is

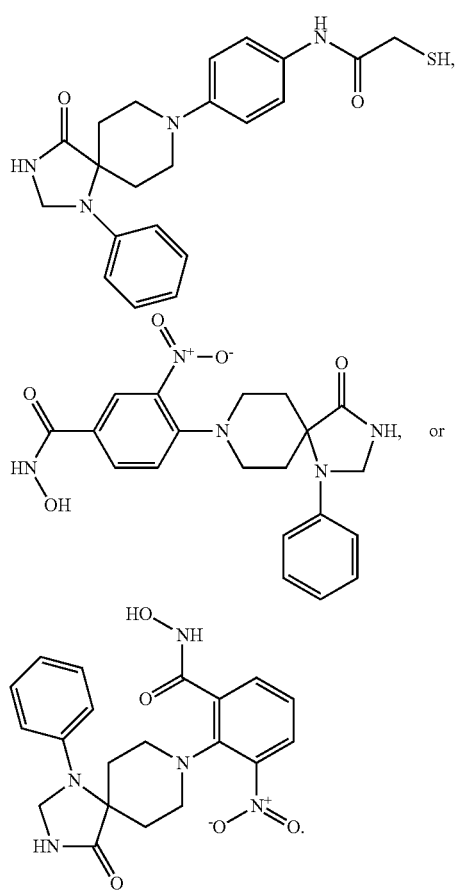

4. A pharmaceutical composition comprising pharmaceutically acceptable carriers and as an active ingredient, a therapeutically effective amount of a compound as claimed in claim 1.

5. A process of preparing a pharmaceutical composition as claimed in claim 4 comprising intimately mixing the pharmaceutically acceptable carriers and the compound.

6. A method of treating ovarian carcinoma in a patient comprising administering to the patient a therapeutically effective amount of a compound of claim 1.

7. A process, comprising
reacting an intermediate of formula (II) with an acid, yielding a hydroxamic acid of formula (I-a)

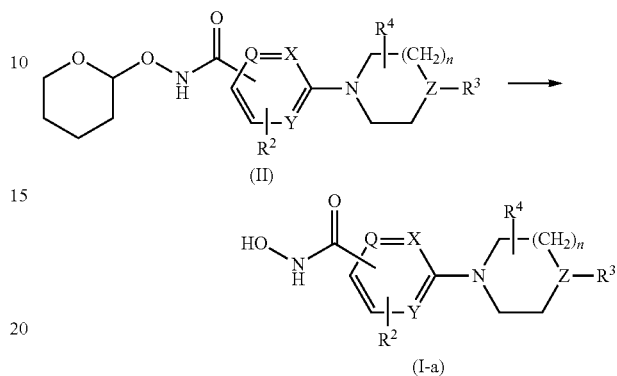

wherein
n is 0, 1, 2 or 3 and when n is 0 then a direct bond is intended;
Q is

X is

Y is

Z is

$R^2$ is hydrogen, halo, hydroxy, amino, nitro, $C_{1-6}$alkyl, $C_{1-6}$alkyloxy, trifluoromethyl, di($C_{1-6}$alkyl)amino, hydroxyamino or naphtalenylsulfonylpyrazinyl;
$R^3$ and $R^4$ are present on the same carbon atom, and $R^3$ and $R^4$ together form a bivalent radical of formula —C(O)—NH—CH$_2$—NR$^{10}$ (a-1)

wherein $R^{10}$ is hydrogen or aryl;
aryl in the above is phenyl, or phenyl substituted with one or more substituents each independently selected from halo, $C_{1-6}$alkyl, $C_{1-6}$alkyloxy, trifluoromethyl, cyano or hydroxycarbonyl.

8. A method of detecting or identifying a histone deactylase (HDAC) in a biological sample comprising detecting or measuring the formation of a complex between a labelled compound as defined in claim 1 and a HDAC.

9. A combination comprising a compound of claim 1 and another anti-cancer agent.

10. The process of claim 7, wherein the acid is trifluoro acetic acid.

11. The compound as claimed in claim 1 wherein $R^1$ is —C(O)NR$^5$R$^6$, —C(O)—C$_{1-6}$alkanediylSR$^7$, —NR$^8$C(O)N(OH)R$^7$, —NR$^8$C(O)C$_{1-6}$alkanediylSR$^7$, or —NR$^8$C(O)C=N(OH)R$^7$ wherein R$^5$ and R$^6$ are each independently hydrogen, hydroxy, hydroxyC$_{1-6}$alkyl or aminoC$_{1-6}$alkyl; and $R^2$ is hydrogen, halo, hydroxy, amino, nitro, C$_{1-6}$alkyl, C$_{1-6}$alkyloxy, trifluoromethyl or di(C$_{1-6}$alkyl)amino.

12. The compound as claimed in claim 1 wherein n is 0 or 1;

each $R^1$ is —C(O)NH(OH) or —NHC(O)C$_{1-6}$alkanediylSH; and $R^2$ is hydrogen or nitro.

13. The compound as claimed in claim 1 wherein n is 1;

$R^1$ is —C(O)NH(OH); and $R^2$ is hydrogen.

* * * * *